United States Patent [19]
Unger et al.

[11] Patent Number: 5,830,430
[45] Date of Patent: Nov. 3, 1998

[54] CATIONIC LIPIDS AND THE USE THEREOF

[75] Inventors: Evan C. Unger; Dekang Shen; Guanli Wu, all of Tucson, Ariz.

[73] Assignee: ImaRx Pharmaceutical Corp., Tucson, Ariz.

[21] Appl. No.: 391,938

[22] Filed: Feb. 21, 1995

[51] Int. Cl.$^6$ .......................... A61K 9/127; G01N 33/92; C07K 17/04; C07H 21/04

[52] U.S. Cl. ................... 424/1.21; 424/283.1; 424/450; 436/71; 436/829; 530/300; 536/23.1

[58] Field of Search .................................. 424/283.1, 450, 424/1.21; 435/71; 436/71, 829; 536/23.1; 530/300

[56] References Cited

U.S. PATENT DOCUMENTS

| | | | |
|---|---|---|---|
| 3,015,128 | 1/1962 | Sommerville et al. | 425/5 |
| 3,293,114 | 12/1966 | Kenaga et al. | 162/168 |
| 3,479,811 | 11/1969 | Walters | 57/153 |

(List continued on next page.)

FOREIGN PATENT DOCUMENTS

| | | |
|---|---|---|
| 641363 | 3/1990 | Australia . |
| B-30351/89 | 3/1993 | Australia . |
| 0 107 559 | 5/1984 | European Pat. Off. . |
| 0 077 752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1 | 3/1990 | European Pat. Off. . |
| 0 361 894 | 4/1990 | European Pat. Off. . |
| 0 216 730 | 1/1991 | European Pat. Off. . |
| 0 467 031 A2 | 5/1991 | European Pat. Off. . |
| 441468 A2 | 8/1991 | European Pat. Off. . |

(List continued on next page.)

OTHER PUBLICATIONS

Desir et al., "Assessment of regional myocardial perfusion with myocardial contrast echocardiography in a canine model of varying degrees of coronary stenosis", *Am. Heart J.*, Jan., 1994, 127(1), 56–63.

Sekins et al., "Lung Cancer Hyperthermia via Ultrasound and PFC Liquids", *Published in Proceedings of 5th International Symposium on Hyperthermic Oncology, Kyoto, Japan*, Aug. 29–Sep. 3, 1998, 3 pages.

Pietersen, "A New Warning System for Fires of Electrical Origin", *CERN European Organization for Nuclear Research, Health and Safety Division*, Mar., 1977, 1–5.

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

Feinstein, Steven B., "Myocardial Perfusion Imaging: Contrast Echocardiography Today and Tomorrow," *Journal of the American College of Cardiology*, 8(1):251–253 (1986).

Keller et al., "The Behavior of Sonicated Albumin Microbubbles Within the Microcirulation: A Basis for Their Use During Myocardial Contrast Echocardiography", *Circulation Res.*, 65(2):458–465 (1989).

Lincoff et al., "Perfluoro–n–butane: A Gas for Maximum Duration Retinal Tamponade," *Arch Ophthalmology*, 101:460–462 (1983).

*Remington's Pharmaceutical Sciences*, John Hoover, managing ed., Mack Publishing Company, Easton, PA, pp. 295–298; 736; 1242–1244 (1975).

(List continued on next page.)

*Primary Examiner*—James Ketter
*Assistant Examiner*—William Sandals
*Attorney, Agent, or Firm*—Woodcock Washburn Kurtz Mackiewicz & Norris LLP

[57] ABSTRACT

Cationic lipid compounds which comprise at least two cationic groups. The cationic lipid compounds are particularly suitable for use as carriers in the intracellular delivery of bioactive agents, including pharmaceuticals and genetic material. Compositions of the present cationic lipid compounds include suspensions, emulsions, micelles and liposomes.

143 Claims, 2 Drawing Sheets

U.S. PATENT DOCUMENTS

| | | | |
|---|---|---|---|
| 3,488,714 | 1/1970 | Walters et al. | 428/321.5 |
| 3,532,500 | 10/1970 | Priest et al. | 430/197 |
| 3,594,326 | 7/1971 | Himmel et al. | 427/213.32 |
| 3,615,972 | 10/1971 | Morehouse et al. | 156/79 |
| 3,650,831 | 3/1972 | Jungermann et al. | 134/27 |
| 3,732,172 | 5/1973 | Herbig et al. | 427/213.32 |
| 3,873,564 | 3/1975 | Schneider et al. | 548/344.1 |
| 3,945,956 | 3/1976 | Garner | 521/88 |
| 3,960,583 | 6/1976 | Netting et al. | 106/122 |
| 3,968,203 | 7/1976 | Spitzer et al. | 424/47 |
| 4,027,007 | 5/1977 | Messina | 424/46 |
| 4,089,801 | 5/1978 | Schneider | 264/4.1 |
| 4,108,806 | 8/1978 | Cohrs et al. | 521/54 |
| 4,138,383 | 2/1979 | Rembaum et al. | 524/809 |
| 4,162,282 | 7/1979 | Fulwyler et al. | 264/9 |
| 4,179,546 | 12/1979 | Garner et al. | 521/56 |
| 4,192,859 | 3/1980 | Mackaness et al. | 424/9.45 |
| 4,224,179 | 9/1980 | Schneider | 264/4.1 |
| 4,229,360 | 10/1980 | Schneider et al. | 264/4.6 |
| 4,265,251 | 5/1981 | Tickner | 600/438 |
| 4,276,885 | 7/1981 | Tickner et al. | 424/9.52 |
| 4,310,505 | 1/1982 | Baldeschwieler et al. | 424/1.21 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,342,826 | 8/1982 | Cole | 435/7.9 |
| 4,344,929 | 8/1982 | Bonsen et al. | 424/15 |
| 4,420,442 | 12/1983 | Sands | 264/13 |
| 4,421,562 | 12/1983 | Sands et al. | 106/603 |
| 4,426,330 | 1/1984 | Sears | 554/80 |
| 4,428,924 | 1/1984 | Millington | 424/9.41 |
| 4,442,843 | 4/1984 | Rasor et al. | 424/9.52 |
| 4,466,442 | 8/1984 | Hilmann et al. | 128/653.1 |
| 4,533,254 | 8/1985 | Cook et al. | 366/176 |
| 4,534,899 | 8/1985 | Sears | 554/80 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon | 424/137 |
| 4,572,203 | 2/1986 | Feinstein | 424/9.52 |
| 4,586,512 | 5/1986 | Do-huu et al. | 128/660.03 |
| 4,603,044 | 7/1986 | Geho et al. | 424/9.52 |
| 4,615,879 | 10/1986 | Runge et al. | 424/9.52 |
| 4,620,546 | 11/1986 | Aida et al. | 128/660.03 |
| 4,646,756 | 3/1987 | Watmough et al. | 607/154 |
| 4,657,756 | 4/1987 | Rasor et al. | 424/9.52 |
| 4,658,828 | 4/1987 | Dory | 128/660.03 |
| 4,675,310 | 6/1987 | Chapman et al. | 514/6 |
| 4,681,119 | 7/1987 | Rasor et al. | 424/9.52 |
| 4,684,479 | 8/1987 | D'Arrigo | 252/307 |
| 4,689,986 | 9/1987 | Carson et al. | 73/19.03 |
| 4,718,433 | 1/1988 | Feinstein | 424/9.52 |
| 4,728,575 | 3/1988 | Gamble et al. | 424/9.321 |
| 4,728,578 | 3/1988 | Higgins et al. | 428/462 |
| 4,731,239 | 3/1988 | Gordon | 424/9.52 |
| 4,737,323 | 4/1988 | Martin et al. | 264/4.3 |
| 4,774,958 | 10/1988 | Feinstein | 424/9.52 |
| 4,775,522 | 10/1988 | Clark, Jr. | 424/9.52 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 424/1.29 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,844,882 | 7/1989 | Widder et al. | 424/9.52 |
| 4,863,717 | 9/1989 | Keana | 424/9.52 |
| 4,865,836 | 9/1989 | Long, Jr. | 424/9.4 |
| 4,877,561 | 10/1989 | Iga et al. | 264/4.3 |
| 4,893,624 | 1/1990 | Lele | 601/3 |
| 4,895,719 | 1/1990 | Radhakrishnan | 424/45 |
| 4,897,355 | 1/1990 | Eppstein et al. | 435/172.3 |
| 4,898,734 | 2/1990 | Mathiowitz et al. | 424/426 |
| 4,900,540 | 2/1990 | Ryan et al. | 424/9.52 |
| 4,921,706 | 5/1990 | Roberts et al. | 424/450 |
| 4,927,623 | 5/1990 | Long, Jr. | 424/9.52 |
| 4,933,121 | 6/1990 | Law et al. | 264/4.3 |
| 4,938,947 | 7/1990 | Nicolau et al. | 424/1.1 |
| 4,946,787 | 8/1990 | Eppstein et al. | 264/4.1 |
| 4,957,656 | 9/1990 | Cerny et al. | 252/311 |
| 4,981,692 | 1/1991 | Popescu et al. | 424/422 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/9.37 |
| 4,996,041 | 2/1991 | Arai et al. | 424/9.52 |
| 5,000,960 | 3/1991 | Wallach | 424/450 |
| 5,004,611 | 4/1991 | Leigh | 424/450 |
| 5,008,050 | 4/1991 | Cullis et al. | 264/4.3 |
| 5,013,556 | 5/1991 | Woodle et al. | 424/450 |
| 5,019,370 | 5/1991 | Jay et al. | 424/9.4 |
| 5,045,304 | 9/1991 | Schneider et al. | 424/9.52 |
| 5,049,388 | 9/1991 | Knight et al. | 424/450 |
| 5,078,994 | 1/1992 | Nair et al. | 424/501 |
| 5,088,499 | 2/1992 | Unger | 424/9.51 |
| 5,100,662 | 3/1992 | Bolcsak et al. | 424/450 |
| 5,114,703 | 5/1992 | Wolf et al. | 424/9.32 |
| 5,123,414 | 6/1992 | Unger | 128/654 |
| 5,135,000 | 8/1992 | Akselrod et al. | 600/458 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9.52 |
| 5,149,319 | 9/1992 | Unger | 604/22 |
| 5,171,678 | 12/1992 | Behr et al. | 435/172.3 |
| 5,171,755 | 12/1992 | Kaufman | 514/759 |
| 5,186,922 | 2/1993 | Shell et al. | 424/9.4 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9.52 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,227,481 | 7/1993 | Tsai et al. | 536/18.7 |
| 5,228,446 | 7/1993 | Unger et al. | 424/9.51 |
| 5,230,882 | 7/1993 | Unger | 424/9.51 |
| 5,247,935 | 9/1993 | Cline et al. | 600/411 |
| 5,264,618 | 11/1993 | Felgner et al. | 560/224 |
| 5,271,928 | 12/1993 | Schneider et al. | 424/9.2 |
| 5,279,833 | 1/1994 | Rose | 424/450 |
| 5,281,408 | 1/1994 | Unger | 424/9.4 |
| 5,283,185 | 2/1994 | Epand et al. | 435/172.3 |
| 5,305,757 | 4/1994 | Unger et al. | 128/662.02 |
| 5,310,540 | 5/1994 | Giddey et al. | 424/9.52 |
| 5,315,997 | 5/1994 | Widder et al. | 128/653.3 |
| 5,315,998 | 5/1994 | Tachibana et al. | 601/2 |
| 5,316,771 | 5/1994 | Barenholz et al. | 424/450 |
| 5,334,381 | 8/1994 | Unger | 424/9.52 |
| 5,334,761 | 8/1994 | Gebeyehu et al. | 564/197 |
| 5,344,930 | 9/1994 | Riess et al. | 544/84 |
| 5,350,571 | 9/1994 | Kaufman et al. | 424/9.52 |
| 5,352,435 | 10/1994 | Unger | 424/9.52 |
| 5,354,549 | 10/1994 | Klaveness et al. | 424/3 |
| 5,358,702 | 10/1994 | Unger | 424/9.322 |
| 5,362,478 | 11/1994 | Desai et al. | 424/322 |
| 5,380,519 | 1/1995 | Schneider et al. | 424/9.52 |
| 5,393,524 | 2/1995 | Quay | 424/9.52 |
| 5,409,688 | 4/1995 | Quay | 424/9.52 |

| Patent No. | Date | Inventor | Class |
|---|---|---|---|
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,547,656 | 8/1996 | Unger | 424/9.4 |
| 5,552,133 | 9/1996 | Lambert et al. | 424/9.52 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,558,856 | 9/1996 | Klaveness et al. | 424/9.37 |
| 5,560,364 | 10/1996 | Porter | 128/662.02 |
| 5,562,893 | 10/1996 | Lohrmann | 424/9.52 |
| 5,567,412 | 10/1996 | Klaveness et al. | 424/9.51 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,449 | 10/1996 | Klaveness et al. | 424/9.51 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,595,723 | 1/1997 | Quay | 424/9.5 |
| 5,605,673 | 2/1997 | Schutt et al. | 424/9.51 |
| 5,606,973 | 3/1997 | Lambert et al. | 128/662.02 |
| 5,614,169 | 3/1997 | Klaveness et al. | 424/9.52 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,672,585 | 9/1997 | Pierschbacher et al. | 514/11 |
| 5,676,928 | 10/1997 | Klaveness et al. | 424/9.321 |
| 5,686,060 | 11/1997 | Schneider et al. | 424/9.52 |
| 5,707,606 | 1/1998 | Quay | 424/9.52 |
| 5,707,607 | 1/1998 | Quay | 424/9.52 |
| B1 4,229,360 | 11/1991 | Schneider et al. | 264/4.6 |

FOREIGN PATENT DOCUMENTS

| | | |
|---|---|---|
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 0 727 225 A2 | 8/1996 | European Pat. Off. . |
| 4028139 A | 3/1992 | Germany ............ A61K 49/02 |
| 62-286534 SHO | 12/1987 | Japan . |
| 63-60943 | 3/1988 | Japan . |
| 1044680 | 10/1966 | United Kingdom . |
| 2193095 | 2/1988 | United Kingdom . |
| WO 80/02365 | 11/1980 | WIPO . |
| WO 82/01642 | 5/1982 | WIPO . |
| US85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/17514 | 10/1992 | WIPO . |
| WO 92/21382 | 10/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 94/06477 | 3/1994 | WIPO . |
| WO 94/07539 | 4/1994 | WIPO . |
| WO 94/09829 | 5/1994 | WIPO . |
| WO 94/16739 | 8/1994 | WIPO . |
| WO 94/21302 | 9/1994 | WIPO . |
| WO 94/28780 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 96/04018 | 2/1996 | WIPO . |
| WO 96/09793 | 4/1996 | WIPO . |
| WO 96/36286 | 11/1996 | WIPO . |

OTHER PUBLICATIONS

*Handbook of Pharmaceutical Excipients*, American Pharmaceutical Association, Washington, D.C. and The Pharmaceutical Society of Great Britain, London, England, pp. 181–183 (1986).

Barnhart et al., "Characteristics of ALBUNEX™: Air–Filled Microspheres for Echocardiography Contrast Enhancement," *Investigative Radiology*, 25:S162–164.

Levene et al., "Characterization of ALBUNEX™," *J. Acoust. Soc. Am.*, 87(Suppl.1 ):569–70.

Miller et al., "Physiochemical Approaches to the Mode of Action of General Anesthetics," *J. Amer. Soc. Anesthesiologists*, 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Lincoff et al., "Intravitreal Expansion of Perfluorocarbon Bubbles", *Arch. Ophthalmol.*, 1980, 98, 1646.

Lincoff et al., "Intravitreal Longevity of Three Perfluorocarbon Gases", *Arch. Ophthalmol.*, 1980, 98, 1610–1611.

Lincoff et al., "The Perfluorocarbon Gases in the Treatment of Retinal Detachment", *Ophthalmology*, 1983, 90(5), 546–551.

Gardner et al., "A Survey of Intraocular Gas Use in North America", *Arch. Ophthalmol.*, 1988, 106, 1188–1189.

Unger et al., "Liposomal MR Contrast Agents", *J. Liposome Research*, 1994, 4(2), 811–834.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. 575–578 (1986).

Chang et al., "Semipermeable Aqueous Microcapsules", *Canadian J. Of Phys. And Pharm.*, 1966, 44, 115–128.

Chang, "Semipermeable Microcapsules", *Science*, 1964, 146, 524–525.

Deasy, *Microencapsulation and Related Drug Processes*, 1983, vol. 20, Chs. 9 and 10, 195–240 (Marcel Dekker, Inc., NY).

Yeung et al., "Preparation of Microencapsulated Liposomes", *J. Microencapsulation*, 1988, 5, 331–337.

Mattrey et al., Gas Emulsions as Ultrasound Contrast Agents; Preliminary Results in Rabbits and Dogs, *Investigative Radiology*, vol. 29, Jun. Supp. 2, pp. S139–S141, 1994.

Meltzer et al., Transmission of Ultrasonic Contrast Through the Lungs, *Ultrasound in Med. & Biol.*, vol. 7, No. 4, 377–384, 1981.

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 29–35, 51–65 and 79–107 (CRC Press Inc., Boca Raton, FL, 1984).

Madden et al., *Chemistry and Physics of Lipids*, vol. 53, pp. 37–46 (1990).

Sinkula et al., *J. Pharm. Sci.*, vol. 64, pp. 181–210 (1975).
Shiina et al., "Hyperthermiaby Low–frequency Synthesized Ultrasound", *IEEE Engineering*, pp. 879–880, vol. 2 (1988) (abstract).
McAvoy et al., *IEEE Engineering, Ultrasonics Symposium Proceedings*, vol. 2, pp. 677–1248 (1989) (abstract).
Chapman et al., "Biomembrane Phase Transitions", *J. Biol. Chem.*, 1974, 249:2512–2521.
Hug et al., "Liposomes for the Transformation of Eukaryotic Cells", *Biochimica et Biophysica Acta*, 1991, 1097:1–17.
Marsh, *CRC Handbook of Lipid Bilayers* (CRC Press, Boca Raton, FL 1990) pp. 139–141.
Szoka et al., "Procedure for Preparation of Liposomes With Large Internal Aqueous Space . . . ", *Proc. Natl. Acad. Sci.* 1978, 75:4194–4198.
Acoustic Imaging; AI5200; Convex Curved Linear Array Ultrasound Transducers Operator's Manual, Nov. 20, 1989, 4700–0003–1C, p. 4.
Bangham et al., "Diffusion of Univalent Ions across the Lamellae of Swollen Phospholipids", *J. Mol. Biol.*, 1965, 13:238–252.
Carson et al., *Ultrasound in Med. & Biol.* 3, 1978, 341–350.
Kost et al., *Polymers in Medicine II: Biomedical and Pharmaceutical Applications*, (Plenum Press, New York and London) pp. 387–396.
deGier et al., "Relations Between Liposomes and Biomembranes", *Annals of The New York Academy of Sciences*, 1978, 308:85–99.
Gabizon et al., "Liposome formulations with prolonged circulation time in blood and enhanced uptake by tumors", *Proc. Natl. Acad. Sci.*, 1988, 85:6949–6953.
Garelli, et al., *Biochimica et Biophysica Acta*, vol. 1127:41–48 (1992).
Kawai et al., "New Procedure for DNA Transfection with Polycation and Dimethyl Sulfoxide", *Molecular and Cellular Biology*, 1984, 4:1172–1174.
Kuo et al., "Metallocene Antitumor Agents. Solution and Solid–State Molybdenocene Coordination . . . ", *J. Am. Chem. Soc.*, 1991, 113:9027–9045.
*Mammalian Cell Biotechnology: A Practical Approach*, M. Butler, 1991 (Oxford University Press, New York), pp. 57–70.
Mathiowitz et al., "Photochemical Rupture of Microcapsules: A Model System", *Journal of Applied Polymer Science*, 1981, 26:809–822.
May et al., "Cationic Liposomes Enable Bovine Herpesvirus Type 2 DNA to Infect Cells", *Acta virol.*, 1991, 35:107.
Poznansky et al., "Biologica Approaches to the Controlled Delivery of Drugs: A Critical Review", *Pharmacol, Rev.*, 1984, 36:277–336.
Sato et al., "Recent Aspects in the Use of Liposomes in Biotechnology and Medicine", *Prog. Lipid Res.* 1992, 4:345–372.
Simons et al., "Antisense c–myb oligonucleotides inhibit intimal arterial smooth muscle cell accumulation in vivo", *Nature*, 1992, 359:67–70.
Trubetskoy et al. "Cationic liposomes enhance targeted delivery and expression of exogenous DNA . . . ", Biochimica et Biophysica Acta 1992, 131:311–313.
Umemura et al., "Studies on Sonodynamic Cancer Therapy", *IEEE*, 1992, O–7803–0785, pp. 354–355.
Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.
Zhou et al., "Targeted delivery of DNA by liposomes and polymers", *J. of Controlled Release* 1992, 19:269–274.
Mathiowitz et al., "Polyanhydride Microspheres as Drug Carriers", *Journal of Applied Polymer Science*, vol. 35, pp. 755–774 (1988).
Sankaram et al., "Cholesterol–Induced Fluid–Phase Immiscibility in Membranes", *Proc. Natl. Acad. Sci.*, vol. 88, pp. 8686–8690 (1991).
*Scientific Apparatus Catalog 92/93* (VWR Scientific, 1991), "Syringes", pp. 1511–1513; Filtration, Syringe Filters, pp. 766–768; Filtration, Membranes, pp. 750–753; Filtration, Filter Holders, p. 744.
Gramiak et al., *Radiology*, "Detection of Intracardiac Blood Flow by Pulsed Echo–Ranging", pp. 415–418 (1971).
Feigenbaum et al., *Circulation*, "Identification of Ultrasound Echoes from the Left Ventricle by Use of Intracardiac Injections of Indocyanine Green", vol. XL1, pp. 615–621 (1970).
Santaella, et al., *FEBS 13463*, "Extended In Vivo Blood Circulation Time of Fluorinated Liposomes", vol. 336, No. 3, pp. 481–484 (1993).
Brown and Langer, *Annual Review Medicine*, 1988, 39:221 29, Annual Review, Inc., "Transdermal Delivery of Drugs", pp. 221–229.
Moseley, et al., *Microbubbles: A Novel MR Susceptibility Contrast Agent*, abstract, 1991 Napa, California Meeting of the Society for Magnetic Resonance in Medicine.
Ter–Pogossia *Tomography*, Kee, et al., n, "Physical Principles and Instrumentation", Computed Body eds., Raven Press, New York, Chapter 1, pp. 1–7 (1988).
Aronberg, "Techniques", *Computed Body Tomography*, Kee, et al., eds., Raven Press, New York, Chapter 2, pp. 9–36 (1988).
Miller, *Ultrasonics* (Sep. 1981), "Ultrasonic detection of resonant cavitation bubbles in a flow tube by their second–harmonic emissions," pp. 217–224.
Dittrich, "Cardiac Muscle Ischemia and Infarction", *The Second Annual International Symposium on Contrast Agents in Diagnostic Ultrasound*, Atlantic City, NJ (May 7, 1996) (abstract).
Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996) (abstract).
Schutt et al., "Osmotically Stabilized Microbubble Sonographic Contrast Agents", *Acad. Radiol.*, vol. 3, Suppl. 2, pp. S188–S190 (Aug. 1996).
Frézard, et al., "Permeability and stability in buffer and in human serum of fluorinated phospholipid–based liposomes", *Biochimica et Biophysica Acta*, 1192, pp. 61–70 (1994).
Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).
Felgner, J. et al., "Enhanced Gene Delivery and Mechanism Studies with a Novel Series of Cationic Lipid Formulations", *The J. Of Biol. Chem.* 1994, 269(4), 2550–2561.
San, H. et al., "Safety and Short–Term Toxicitiy of a Novel Cationic Lipid Formulation for Human Gene Therapy", *Human Gene Therapy* 1993, 4, 781–788.

Baker, G. and Rhodes, C., eds., *Modern Pharmaceutics*, Marcel Dekker Inc., New York, NY, 1990.

Barthel, F. et al., "Laboratory Methods: Gene transfer optimization with liposperimine–Coated DNA", *DNA and Cell Biology*, 1993, 12, 553–560.

Behr, J. et al., "Efficient gene transfer into mammalian primary endocrine cells with lipopolyamine–caoted DNA", *PNAS USA* 1989, 86, 6982–6986.

Canfield et al., "Incorporation of β–Carotene into Mixed Micelles", *Methods in Enzymology* 1990, 189, 418–422.

Cheng et al., "The Production and Evaluation of Contrast–Carrying Liposomes Made with an Automatic High–Pressure System", *Investigative Radiology*, 1987, 22, 47–55.

El–Gorab et al., "Solubilization of β–Carotene and Retinol Into Aqueous Solutions of Mixed Micelles", *Biochem. Biophys. Acta* 1973, 306, 58–66.

Felgner, et al., "Lipofection: A Highly Efficient, Lipid–Mediated DNA–Transfection Procedure", *PNAS USA* 1987, 84, 7413–7417.

Fendler and Fendler, *Catalysis in Micellar and Macromolecular Systems*, Academic Press, NY, 1975.

Fitzpatrick et al., "Metal Ion Decarboxylation. Kinetics and Mechanism of the Oxidative Decarboxylation of Copper(II) Complexes of Aminomalonic Acid in Aqueous Solution", *Inorganic Chemistry* 1974, 13(3), 568–574.

Gaentzler et al., "Perfluoroalkylated Phosphocholines. Improved Synthesis, Surface Activity, Fluorocarbon Emulsifying Capability and Biological Properties", *New Journal of Chemistry* 1993, 17(5), 337–344.

Gregoriadis, G., ed., *Liposome Technology*, vol. I, pp. 29–35, 51–65 and 79–107, CRC Press, Boca Raton, FL 1984.

Hope et al., "Production of Large Unilamellar Vesicles By a Rapid Extrusion Procedure. Characterization of Size Distribution, Trapped Volume and Ability to Maintain a Membrane Potential", *Biochimica et Biophysica Acta* 1985, 812, 55–65.

Ishihara et al., "Effects of Phospholipid Adsorption on Nonthrombogenicity of Polymer with Phospholipid Polar Group", *Journal of Biomedical Materials Research* 1993, 27, 1309–1314.

Loeffler, J., "Lipopolyamine–Mediated Transfection Allows Gene Expression Studies in Primary Neuronal Cells", *J. Neurochem.* 1990, 54, 1812–1815.

Mayer et al., "Vesicles of Variable Sizes Produced By A Rapid Extrusion Procedure", *Biochimica et Biophysica Acta* 1986, 858, 161–168.

Mayhew et al., "Characterization of Liposomes Prepared Using a Microemulsifier", *Biochimica et Biophysica Acta*, 1984, 775, 169–74.

Mayhew et al., "High–Pressure Continuous–Flow System for Drug Entrapment in Liposomes", *Methods in Enzymology* 1987, 149, 64–77.

Santaella, C. et al., "Emulsification of Fluorocarbons Using Perfluoroalkylated Glycerophosphocholines as Surfactants or Co–Surfactants", *New Journal of Chemistry* 1992, 16(3), 399–404.

Shinoda, K., Nakagana, Tamamushi and Isemura, *Colloidal Surfactant*, Academic Press, 1963, especially "The Formation of Micelles", Shinoda, Chapter 1, pp. 1–96.

Solé–Violan, L., "Partition Coefficients of Mixed Fluorocarbon–Hydrocarbon Compounds Between Fluorocarbons and Hexadecane. Relevance to Fluorocarbon Emulsion Stabilization", *New Journal of Chemistry* 1993, 17(8,9), 581–583.

Stel'mashok et al., "Photolysis of Frozen Solutions of Malonate Complexes of Manganese (III)", Institute of Physics, Academy of Sciences of the Belorussian SSR, pp. 401–404. (Translated from *Koordinatsionnaya Khimia* 1977, 3(4), 524–527.

Szoka and Papahadjopoulos, "Comparative Properties and Methods of Preparation of Lipid Vesicles (Liposomes)", *Ann. Rev. Biopohysic. Bioeng.* 1980, 9, 467–508.

Thanassi, "Aminomalonic Acid. Spontaneous Decarboxylation and Reaction with 5–Deoxypyridoxal", *Biochemistry* 1970, 9(3), 525–532.

Thompson, L., "At age 2, gene therapy enters a growth phase", *Science* 1992, 258, 744–746.

U.S. Pharmacopeia, USP XXII, NF XVII, The United States Pharmacopeia, The National Formulary, United States Pharmacopeial Convention Inc., 12601 Twinbrook Parkway, Rockville, MD 20852.

Zhou and Huang, "DNA Transfection Mediated by Cationic Liposomes Containing Lipopolylysine: Characterization and Mechanism of Action", *Biochimica et Biophysica Acta* 1994, 1189, 195–203.

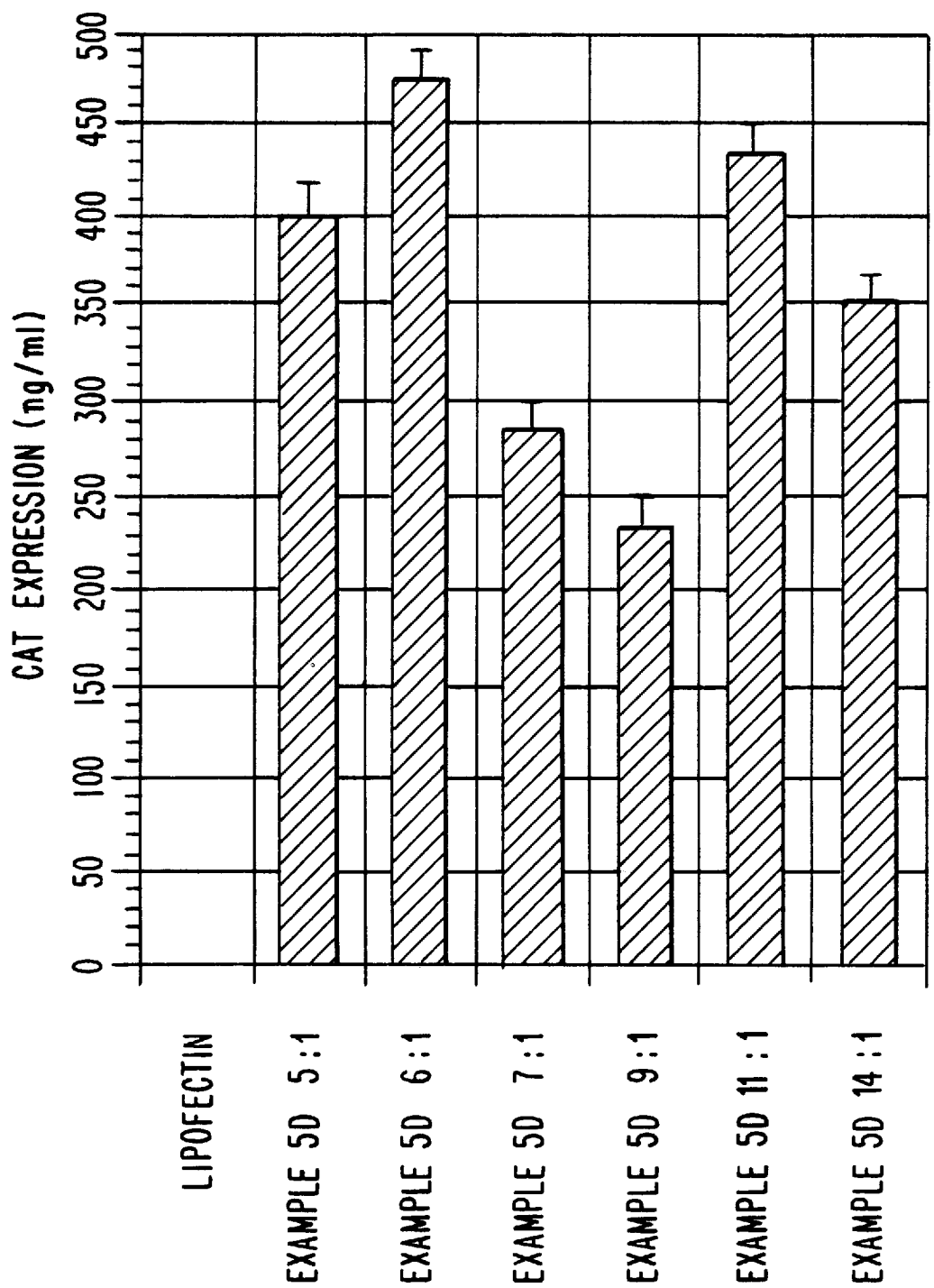

5,830,430

CATIONIC LIPIDS AND THE USE THEREOF

FIELD OF THE INVENTION

The present invention relates to novel cationic lipids and the use thereof. More particularly, the present invention relates to novel cationic lipids and their use in the delivery of biologically active agents.

BACKGROUND OF THE INVENTION

The intracellular delivery of biologically active agents, for example, pharmacologically active materials and diagnostic agents, is generally desirable in connection with the treatment and/or diagnosis of various diseases. For example, cell function can be influenced at the subcellular or molecular level by delivering the biologically active agent intracellularly.

Various methods have been developed for the delivery of biologically active agents directly into living cells. Included among such methods is the "carrier method" which involves the use of a carrier to promote intracellular delivery of a bioactive agent to specifically targeted cells, for example, diseased cells. The intracellular delivery of therapeutic agents is referred to herein also as "transfection".

Various carriers have been developed for use in the transfection of biologically active agents. For example, liposomes and polymers have been developed for the transfection of genetic materials, including deoxyribonucleic acid (DNA) and ribonucleic acid (RNA). However, the currently available carriers, including liposomes and polymers, are generally ineffective for the intracellular delivery of biologically active materials in vivo. Moreover, the currently available carriers have limited use in connection with the transfection of cells in vitro.

In addition to the carrier method, alternative methods have been developed for the transfection of biologically active agents, including genetic material, directly into cells. These methods include, for example, calcium phosphate precipitation and electroporation. However, these methods are also generally ineffective for the intracellular delivery of biologically active agents in vivo.

Great strides have been made in connection with the characterization and understanding of various diseases, for example, genetic diseases, and their associated protein transcription, in humans and other animals. This has led to the development or postulation of improved methods for the treatment of such diseases with biologically active agents. Various of these methods involve or require that the biologically active agent be delivered intracellularly. As noted above, however, current methods for the transfection of cells with biologically active agents in vivo are generally ineffective. This is thwarting the study and implementation of improved methods for the treatment of various diseases.

The cellular membrane is a selective barrier which prevents random introduction of substances into the cell. Accordingly, a major difficulty in the intracellular delivery of biologically active agents is believed to involve the transfer of the agent from the extracellular space to the intracellular space. Localization of the biologically active agent at the surface of selected cell membranes has been difficult to achieve also.

Carriers have been engineered also from viral vectors. Specifically, vectors for the transfection of genetic material have been developed from whole viruses, including adenoviruses and retroviruses. However, only a limited amount of biologically active materials can be placed inside of a viral capsule. Moreover, in the case of biologically active materials which comprise genetic material, undesired interaction of the viral carrier may occur with the encapsulated genetic material and the patient.

To minimize the potential interactions associated with viruses, attempts have been made to use only certain components of a virus. This is difficult to achieve in vivo inasmuch as the virus components must be able to recognize and reach the targeted cells. Despite extensive work, a successfully targeted, viral-mediated vector for the delivery of biologically active materials into cells in vivo has not been adequately achieved.

As noted above, liposomes have been used as a carrier for the intracellular delivery of biologically active agents, including genetic material. One of the original methods for the use of liposomes as carriers for biologically active agents is disclosed in Szoka and Papahadjopoulos, $Ann. Rev. Biophysic. Bioeng.$, Vol. 9, pp. 467–508 (1980). The disclosed method involves the preparation of liposomes by the addition of an aqueous solution of genetic material to phospholipids which are dissolved in ether. Evaporation of the ether phase provides genetic material encapsulated in lipid vesicles.

Another method for encapsulating biologically active agents in liposomes involves the extrusion of dehydration-rehydration vesicles. Other methods, in addition to those described above, are known for the encapsulation by liposomes of biologically active agents.

More recently, liposomes have been developed from cationic lipids, such as N-[1-(2,3-dioleoyloxy)propyl]-N,N,N-trimethylammonium chloride ("DOTMA") or lipids which comprise cationic polymers, for example, polysine. See, e.g., Xiaohuai and Huang, $Biochimica et Biophysica Acta$, Vol. 1189, pp. 195–203 (1994). Liposomes which are prepared from cationic materials (referred to hereinafter as "cationic liposomes") have been developed, inter alia, to transfect cells with genetic material, including DNA. It is believed that the cationic liposomes bind with the negatively charged phosphate group(s) of the nucleotides in DNA. Studies have shown that cationic liposomes mediate transfection of cells with genetic material in vitro more efficiently than other carriers, for example, cationic polymers. In addition, in vitro studies have shown also that cationic liposomes provide improved transfection of cells relative to other delivery methods, including electroporation and calcium phosphate precipitation.

However, the currently available cationic lipids and cationic liposomes are generally ineffective for the intracellular delivery of biologically active agents in vivo. Moreover, they are generally ineffective for the intracellular delivery of biologically active agents in serum. This is a serious drawback inasmuch as cells require serum for viability. In fact, it is generally necessary to remove serum from tissue culture baths during gene transfection studies involving cationic lipids and cationic liposomes. After transfection, the serum is replaced. This involves additional processing steps which render transfection of cells with cationic lipids and cationic liposomes complex and cumbersome.

New and/or better cationic lipids useful, inter alia, for the intracellular delivery of bioactive agents are needed. The present invention is directed to this as well as other important ends.

SUMMARY OF THE INVENTION

The present invention is directed to cationic lipids which comprise at least one, and preferably at least two, cationic groups and which may be useful for the intracellular delivery of bioactive agents.

Specifically, in one embodiment, the present invention relates to a cationic lipid compound of the formula $$Y_1-(R_1-X_1)_x-R_2-[Y_2-R_3]_y-(X_1-R_1)_x-Y_1 \quad \overset{(R_4-Y_3)_z}{|} \quad (I)$$

wherein:

each of x, y and z is independently an integer from 0 to about 100;

each $X_1$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O—C(=X$_2$)— or —X$_2$—(R$_5$X$_2$)P(=X$_2$)—X$_2$—;

each $X_2$ is independently O or S;

each $Y_1$ is independently a phosphate residue, N(R$_6$)$_a$—, S(R$_6$)$_a$—, P(R$_6$)$_a$— or —CO$_2$R$_6$, wherein a is an integer from 1 to 3;

each $Y_2$ is independently —N(R$_6$)$_b$—, —S(R$_6$)$_b$— or —P(R$_6$)$_b$—, wherein b is an integer from 0 to 2;

each $Y_3$ is independently a phosphate residue, N(R$_6$)$_a$—, S(R$_6$)$_a$—, P(R$_6$)$_a$— or —CO$_2$R$_6$, wherein a is an integer from 1 to 3;

each of $R_1$, $R_2$, $R_3$ and $R_4$ is independently alkylene of 1 to about 20 carbons;

each $R_5$ is independently hydrogen or alkyl of 1 to about 10 carbons; and each $R_6$ is independently —[R$_7$—X$_3$]$_c$—R$_8$ or —R$_9$—[X$_4$—R$_{10}$]$_d$—Q, wherein:

each of c and d is independently an integer from 0 to about 100;

each Q is independently a phosphate residue, —N(R$_{11}$)$_q$, —S(R$_{11}$)$_q$, —P(R$_{11}$)$_q$ or —CO$_2$R$_6$, wherein q is an integer from 1 to 3;

each of $X_3$ and $X_4$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O—C(=X$_2$)— or —X$_2$—(R$_5$X$_2$)P(=X$_2$)—X$_2$—;

each $R_7$ is independently alkylene of 1 to about 20 carbons;

each $R_8$ is independently hydrogen or alkyl of 1 to about 60 carbons;

each of $R_9$ and $R_{10}$ is independently alkylene of 1 to about 20 carbons; and each $R_{11}$ is independently —[R$_7$—X$_3$]$_c$—R$_8$ or —R$_9$—[X$_4$—R$_{10}$]$_d$—W, wherein:

each W is independently a phosphate residue, —N(R$_{12}$)$_w$, —S(R$_{12}$)$_w$, —P(R$_{12}$)$_w$ or —CO$_2$R$_6$, wherein w is an integer from 1 to 3; and $R_{12}$ is —[R$_7$—X$_3$]$_{c-R8}$; with the proviso that the compound of formula (I) comprises at least one, and preferably at least two, quaternary salts.

In another embodiment, the invention relates to a cationic lipid compound of the formula $$Y_1-R_1-Y_1 \quad (II)$$

wherein:

each $Y_1$ is independently a phosphate residue, N(R$_2$)$_a$—, S(R$_2$)$_a$—, P(R$_2$)$_a$— or —CO$_2$R$_2$, wherein a is an integer from 1 to 3;

$R_1$ is alkylene of 1 to about 60 carbons containing 0 to about 30 —O—, —S—, —NR$_3$— or —X$_2$—(R$_3$X$_2$)P(=X$_2$)—X$_2$— heteroatoms or heteroatom groups;

$R_2$ is a residue of the formula —R$_4$—[(X$_1$—R$_5$)$_x$—Y$_2$]$_y$—R$_6$, wherein:

each of x and y is independently an integer from 0 to about 100;

each $X_1$ is independently a direct bond, —O—, —S—, —NR$_3$—, —C(=X$_2$)—, —C(=X$_2$)—N(R$_3$)—, —N(R$_3$)—C(=X$_2$)—, —C(=X$_2$)—O—, —O—C(=X$_2$)— or —X$_2$—(R$_3$X$_2$)P(=X$_2$)—X$_2$—;

each $X_2$ is independently O or S;

each $Y_2$ is independently —S(R$_2$)$_b$—, —N(R$_2$)$_b$— or —P(R$_2$)$_b$—, wherein b is an integer from 0 to 2;

each $R_3$ is independently hydrogen or alkyl of 1 to about 10 carbons;

each of $R_4$ and $R_5$ is independently a direct bond or alkylene of 1 to about 30 carbons containing 0 to about 15 —O—, —S—, —NR$_3$— or —X$_2$—(R$_3$X$_2$)P(=X$_2$)—X$_2$— heteroatoms or heteroatom groups; and each $R_6$ is independently hydrogen or alkyl of 1 to about 60 carbons containing 0 to about 30 —O—, —S—, —NR$_3$— or —X$_2$—(R$_3$X$_2$)P(=X$_2$)—X$_2$— heteroatoms or heteroatom groups; with the proviso that the compound of formula (II) comprises at least one, and preferably at least two, quaternary salts.

In yet another embodiment, the present invention relates to a cationic lipid compound of the formula

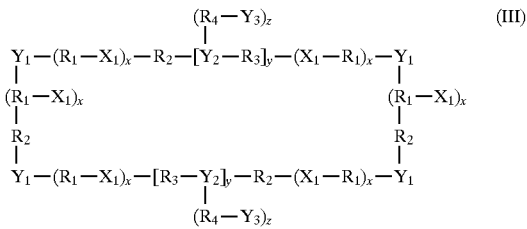

wherein:

each of x, y and z is independently an integer from 0 to about 100;

each $X_1$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O—C(=X$_2$)— or —X$_2$—(R$_5$X$_2$)P(=X$_2$)—X$_2$—;

each $X_2$ is independently O or S;

each $Y_1$ is independently —O—, —N(R$_6$)$_a$—, —S(R$_6$)$_a$— or —P(R$_6$)$_a$—, wherein a is an integer from 0 to 2;

each $Y_2$ is independently —N(R$_6$)$_a$—, —S(R$_6$)$_a$— or —P(R$_6$)$_a$—, wherein a is an integer from 0 to 2;

each $Y_3$ is independently a phosphate residue, N(R$_6$)$_b$—, S(R$_6$)$_b$—, P(R$_6$)$_b$— or —CO$_2$R$_6$, wherein b is an integer from 1 to 3;

each of $R_1$, $R_2$, $R_3$ and $R_4$ is independently alkylene of 1 to about 20 carbons;

each $R_5$ is independently hydrogen or alkyl of 1 to about 10 carbons; and each $R_6$ is independently —[R$_7$—X$_3$]$_c$—R$_8$ or —R$_9$—[X$_4$—R$_{10}$]$_d$—Q, wherein:

each of c and d is independently an integer from 0 to about 100;

each Q is independently a phosphate residue, —N(R$_{11}$)$_q$, —S(R$_{11}$)$_q$, —P(R$_{11}$)$_q$ or —CO$_2$R$_{11}$, wherein q is an integer from 1 to 3;

each of $X_3$ and $X_4$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O—C(=X$_2$)— or —X$_2$—(R$_5$X$_2$)P(=X$_2$)—X$_2$—;

each $R_7$ is independently alkylene of 1 to about 20 carbons;

each $R_8$ is independently hydrogen or alkyl of 1 to about 60 carbons;

each of $R_9$ and $R_{10}$ is independently alkylene of 1 to about 20 carbons; and each $R_{11}$, is independently $-[R_7-X_3]_c-R_8$ or $-R_9-[X_4-R_{10}]_d-W$, wherein:

each W is independently a phosphate residue, $-N(R_{12})_w$, $-S(R_{12})_w$, $-P(R_{12})_w$ or $-CO_2R_{12}$, wherein w is an integer from 1 to 3; and $R_{12}$ is $-[R_7-X_3]_c-R_8$; with the proviso that the compound of formula (III) comprises at least one, and preferably at least two, quaternary salts.

Cationic lipid compounds which comprise at least one, and preferably at least two, cationic groups are also the subject of the present invention.

Another aspect of the present invention are cationic lipid compositions which are composed of cationic lipid compounds that comprise at least one, and preferably at least two, cationic groups.

Yet another aspect of the present invention is a cationic lipid formulation for the intracellular delivery of a bioactive agent. The formulation comprises, in combination with a bioactive agent, a cationic lipid compound that comprises at least one, and preferably at least two cationic groups.

Still another aspect of the present invention relates to a process for the preparation of a cationic lipid formulation for the intracellular delivery of a bioactive agent. The process comprises combining together a bioactive agent and a cationic lipid composition which comprises a cationic lipid compound having at least one, and preferably at least two, cationic groups.

Also encompassed by the present invention is a method for delivering intracellularly a bioactive agent. The method comprises contacting cells with a cationic lipid compound having at least one, and preferably at least two, cationic groups and a bioactive agent.

These and other aspects of the invention will become more apparent from the present specification and claims.

BRIEF DESCRIPTION OF THE DRAWINGS

FIGS. 1 and 2 are graphical representations of the amount of protein expressed in transfection experiments involving cationic lipid compounds of the present invention and compounds disclosed in the prior art.

DETAILED DESCRIPTION OF THE INVENTION

Figure 1:
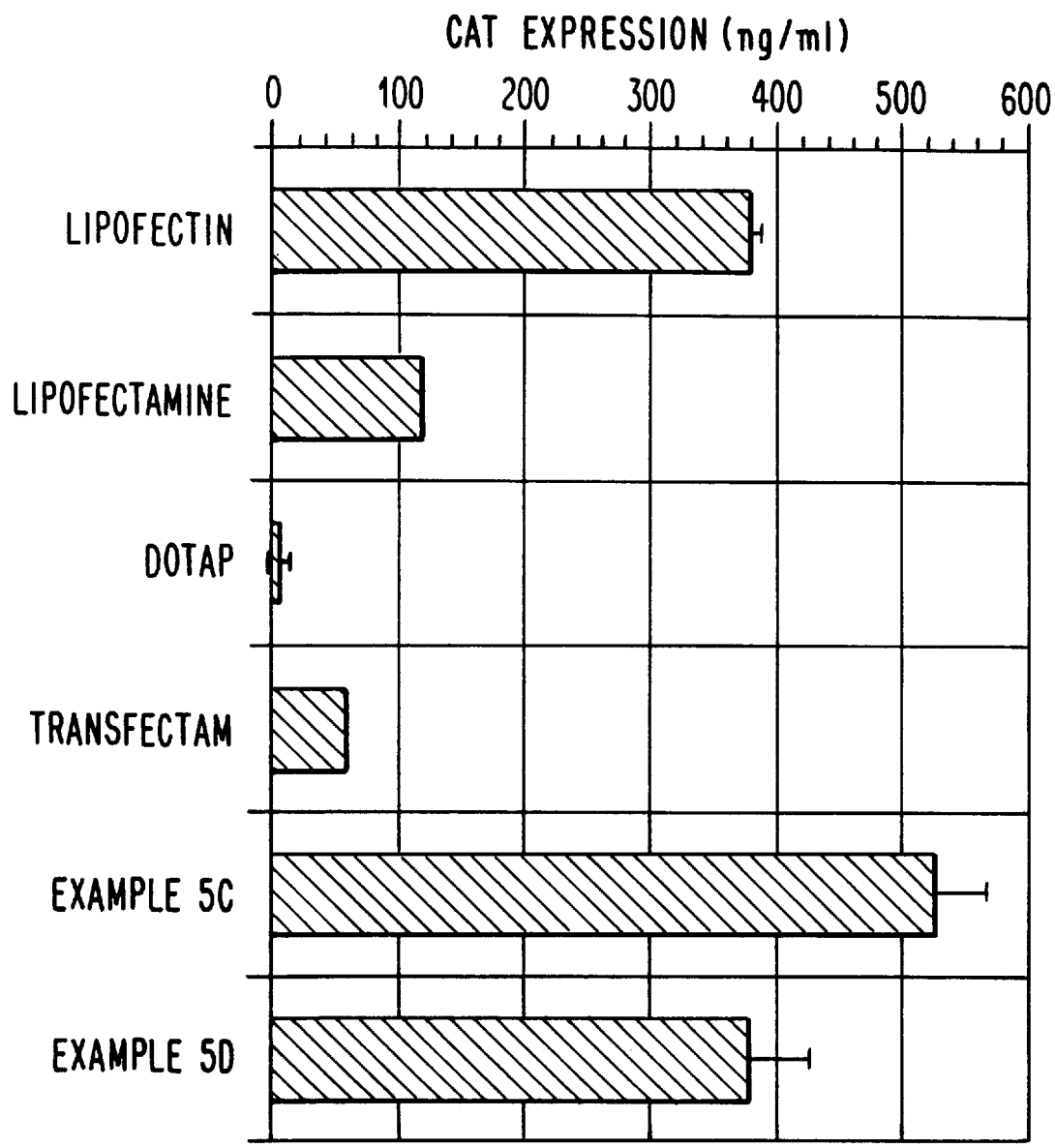

As employed above and throughout the disclosure, the following terms, unless otherwise indicated, shall be understood to have the following meanings.

"Alkyl" refers to an aliphatic hydrocarbon group which may be straight or branched having 1 to about 60 carbon atoms in the chain. "Lower alkyl" refers to an alkyl group having 1 to about 8 carbon atoms. "Higher alkyl" refers to an alkyl group having about 10 to about 20 carbon atoms. The alkyl group may be optionally substituted with one or more alkyl group substituents which may be the same or different, where "alkyl group substituent" includes halo, aryl, hydroxy, alkoxy, aryloxy, alkyloxy, alkylthio, arylthio, aralkyloxy, aralkylthio, carboxy alkoxycarbonyl, oxo and cycloalkyl. There may be optionally inserted along the alkyl group one or more oxygen, sulphur or substituted or unsubstituted nitrogen atoms, wherein the nitrogen substituent is lower alkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Preferred alkyl groups include the lower alkyl groups of 1 to about 4 carbons and the higher alkyl groups of about 12 to about 16 carbons. Preferred alkyl groups include also alkyl groups which are substituted with one or more halo atoms. Fluoroalkyl groups are preferred among the halo-substituted alkyl groups, including, for example, fluoroalkyl groups of the formula $CF_3(CF_2)_n(CH_2)_m-$, wherein each of m and n is independently an integer from 0 to about 22. Exemplary fluoroalkyl groups include perfluoromethyl, perfluoroethyl, perfluoropropyl, perfluorobutyl, perfluorocyclobutyl, perfluoropentyl, perfluorohexyl, perfluoroheptyl, perfluorooctyl, perfluorononyl, perfluorodecyl, perfluoroundecyl and perfluorododecyl.

"Alkenyl" refers to an alkyl group containing at least one carbon-carbon double bond. The alkenyl group may be optionally substituted with one or more "alkyl group substituents". Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon-carbon triple bond. The alkynyl group may be optionally substituted with one or more "alkyl group substituents". Exemplary alkynyl groups include ethynyl, propargyl, n-pentynyl, decynyl and dodecynyl. Preferred alkynyl groups include the lower alkynyl groups.

"Cycloalkyl" refers to a non-aromatic mono- or multicyclic ring system of about 4 to about 10 carbon atoms. The cycloalkyl group may be optionally partially unsaturated. The cycloalkyl group may be also optionally substituted with an aryl group substituent, oxo and/or alkylene. Preferred monocyclic cycloalkyl rings include cyclopentyl, cyclohexyl and cycloheptyl. Preferred multicyclic cycloalkyl rings include adamantyl, octahydronaphthyl, decalin, camphor, camphane, noradamantyl, bicyclo[2.2.2.]oct-5-ene, cis-5-norbornene, 5-norbornene, (1R)-(−)-myrtentane, norbornane and anti-3-oxo-tricyclo[2.2.1.0$^{2,6}$]heptane.

"Aryl" refers to an aromatic carbocyclic radical containing about 6 to about 10 carbon atoms. The aryl group may be optionally substituted with one or more aryl group substituents which may be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, rylthio, alkylthio, alkylene and $-NRR'$, where R and R' are each independently hydrogen, alkyl, aryl and aralkyl. Exemplary aryl groups include substituted or unsubstituted phenyl and substituted or unsubstituted naphthyl.

"Acyl" refers to an alkyl-CO— group wherein alkyl is as previously described. Preferred acyl groups comprise alkyl of 1 to about 30 carbon atoms. Exemplary acyl groups include acetyl, propanoyl, 2-methylpropanoyl, butanoyl and palmitoyl.

"Aroyl" means an aryl-CO— group wherein aryl is as previously described. Exemplary aroyl groups include benzoyl and 1- and 2-naphthoyl.

"Alkoxy" refers to an alkyl-O— group wherein alkyl is as previously described. Exemplary alkoxy groups include methoxy, ethoxy, n-propoxy, i-propoxy, n-butoxy and heptoxy.

"Aryloxy" refers to an aryl-O— group wherein the aryl group is as previously described. Exemplary aryloxy groups include phenoxy and naphthoxy.

"Alkylthio" refers to an alkyl-S— group wherein alkyl is as previously described. Exemplary alkylthio groups include methylthio, ethylthio, i-propylthio and heptylthio.

"Arylthio" refers to an aryl-S— group wherein the aryl group is as previously described. Exemplary arylthio groups include phenylthio and naphthylthio.

"Aralkyl" refers to an aryl-alkyl- group wherein aryl and alkyl are as previously described. Exemplary aralkyl groups include benzyl, phenylethyl and naphthylmethyl.

"Aralkyloxy" refers to an aralkyl-O— group wherein the aralkyl group is as previously described. An exemplary aralkyloxy group is benzyloxy.

"Aralkylthio" refers to an aralkyl-S— group wherein the aralkyl group is as previously described. An exemplary aralkylthio group is benzylthio.

"Dialkylamino" refers to an —NRR' group wherein each of R and R' is independently an alkyl group as previously described. Exemplary alkylamino groups include ethylmethylamino, dimethylamino and diethylamino.

"Alkoxycarbonyl" refers to an alkyl-O—CO— group. Exemplary alkoxycarbonyl groups include methoxycarbonyl, ethoxycarbonyl, butyloxycarbonyl and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl as previously described.

"Dialkylcarbamoyl" refers to R'RN—CO— group wherein each of R and R' is independently alkyl as previously described.

"Acyloxy" refers to an acyl-O— group wherein acyl is as previously described.

"Acylamino" refers to an acyl-NH— group wherein acyl is as previously described.

"Aroylamino" refers to an aroyl-NH— group wherein aroyl is as previously described.

"Alkylene" refers to a straight or branched bivalent aliphatic hydrocarbon group having from 1 to about 30 carbon atoms. The alkylene group may be straight, branched or cyclic. The alkylene group may be also optionally unsaturated and/or substituted with one or more "alkyl group substituents." There may be optionally inserted along the alkylene group one or more oxygen, sulphur or substituted or unsubstituted nitrogen atoms, wherein the nitrogen substituent is alkyl as previously described. Exemplary alkylene groups include methylene (—$CH_2$—), ethylene (—$CH_2CH_2$—), propylene (—$(CH_2)_3$—), cyclohexylene (—$C_6H_{10}$—), —CH═CH—CH═CH—, —CH═CH—$CH_2$—, —$(CF_2)_n(CH_2)_m$—, wherein n is an integer from about 1 to about 22 and m is an integer from 0 to about 22, —$(CH_2)_n$—N(R)—$(CH_2)_m$—, wherein each of m and n is independently an integer from 0 to about 30 and R is hydrogen or alkyl, methylenedioxy (—O—$CH_2$—O—) and ethylenedioxy (—O—$(CH_2)_2$—O—). It is preferred that the alkylene group has about 2 to about 3 carbon atoms.

"Halo" or "halide" refers to fluoride, chloride, bromide or iodide.

"Heteroatom group" refers to a radical which contains at least one heteroatom.

"Amino Acid" refers to a naturally occurring or synthetic amino acid.

"Polypeptide" refers to a biologically active series of two or more amino acid residues bonded by peptide linkages. Polypeptides having about 3 to about 40 amino acid residues are preferred.

"Phosphate residue" refers to a substituent group which is derived from phosphoric acid (O═P(OH)$_3$). Preferably, the phosphate residue is an ester of phosphoric acid which is substituted with one or more alkyl and/or alkenyl groups. Preferred phosphate esters include phospholipids. Preferred among the phospholipids are phosphoglycerides, with diacylglycerol phosphates being especially preferred. An exemplary diacylglycerol phosphate is 1,2-dioleoylglycero-3-phosphoethyl.

"Quaternary salt" refers to a type of ammonium, sulfonium or phosphonium compound in which the hydrogen atoms of the ammonium, sulfonium or phosphonium ion are replaced by alkyl groups. With respect to quaternary ammonium and phosphonium compounds, the molecular structure includes a nitrogen or phosphorous atom joined to four organic groups, for example, alkyl groups. The molecular structure of a quaternary sulfonium compound includes a sulfur atom joined to three organic groups. These molecular structures are positively charged and are generally referred to as cations or cationic groups. The cations are typically, although not necessarily, associated with a negatively charged acid radical. The negatively charged radical is generally referred to as an anion or an anionic group. Exemplary anions include, for example, halides. Quaternary salts are generally the product of the final stage of alkylation of nitrogen, sulfur or phosphorous.

"Lipid" refers to a synthetic or naturally-occurring amphipathic compound which comprises a hydrophilic component and a hydrophobic component. Lipids include, for example, fatty acids, neutral fats, phosphatides, glycolipids, aliphatic alcohols and waxes, terpenes and steroids.

"Cationic lipid compound" refers to a lipid which comprises a cationic group and which functions generally as a positively charged ion, for example, in solution. Preferred cationic lipid compounds are lipids which comprise at least one cationic group, with lipids which comprise at least two or more cationic groups being more preferred.

"Cationic group" refers to a group which is positively charged. Preferred cationic groups include the positively charged ions of quaternary salts. Exemplary quaternary salts are ammonium, phosphonium and sulfonium salts.

"Counter ion" refers to an anion. An anion which is "pharmaceutically-acceptable" is substantially non-toxic and does not render the associated cation pharmaceutically unacceptable.

"Cationic lipid composition" refers to a composition which comprises a cationic lipid compound. Exemplary cationic lipid compositions include suspensions, emulsions, vesicular compositions and hexagonal H II phase structures. "Cationic lipid formulation" refers to a composition which comprises a cationic lipid compound and a bioactive agent.

"Charge density" refers to charge per unit mass or volume.

"Vesicle" or "vesicular species" refers to a spherical entity which is characterized by the presence of an internal void. Preferred vesicles or vesicular species are formulated from lipids, including the cationic lipid compounds of the present invention. In any given vesicle or vesicular species, the lipids may be in the form of a monolayer or bilayer, and the mono- or bilayer lipids may be used to form one or more mono- or bilayers. In the case of more than one mono- or bilayer, the mono- or bilayers are generally,concentric. The lipid vesicles or vesicular species include such entities commonly referred to as liposomes, micelles and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles are generally filled with a liquid, including, for example, an aqueous liquid, a gas, a gaseous precursor, and/or a solid material, including, for example, a bioactive agent.

"Cationic vesicle" or "cationic vesicular composition" refers to a vesicle or vesicular species which is formulated from a cationic lipid compound.

"Cationic vesicle formulation" refers to a composition of a vesicle or vesicular species and a bioactive agent.

"Liposome" refers to a generally spherical cluster or aggregate of amphipathic compounds, including lipid compounds, typically in the form of one or more concentric layers, for example, bilayers.

"Emulsion" refers to a lipoidal mixture of two or more liquids and is generally in the form of a colloid. The lipids may be heterogeneously dispersed throughout the emulsion. Alternatively, the lipids may be aggregated in the form of, for example, clusters or layers, including mono- or bilayers.

"Suspension" refers to a mixture of finely divided colloidal particles floating in a liquid.

"Hexagonal H II phase structure" refers to a generally tubular aggregation of lipids in liquid media, for example, aqueous media, in which the hydrophilic portion(s) of the lipids generally face inwardly in association with a liquid environment inside the tube. The hydrophobic portion(s) of the lipids generally radiate outwardly and the complex assumes the shape of a hexagonal tube. A plurality of tubes is generally packed together in the hexagonal phase structure.

"Patient", as used herein, refers to animals, including mammals, preferably humans.

"Bioactive agent" refers to a substance which is capable of exerting a biological effect in vitro and/or in vivo. The biological effect is preferably therapeutic in nature. As used herein, "bioactive agent" refers also to substances which are used in connection with an application which is diagnostic in nature, such as in methods for diagnosing the presence or absence of a disease in a patient. The bioactive agents may be neutral or positively or negatively charged. Preferably, the bioactive agents are negatively charged. Examples of suitable bioactive agents include pharmaceuticals and drugs, synthetic organic molecules, proteins, vitamins, steroids, polyanions, nucleosides, nucleotides, polynucleotides and diagnostic agents, such as contrast agents for use in connection with magnetic resonance imaging, ultrasound or computed tomography of a patient.

"Anionic group" refers to a group which is negatively charged. Preferred anionic groups include phosphate ($PO_4^-$) groups.

"Anionic bioactive agent" refers to a bioactive agent that comprises at least one anionic group. Certain genetic materials, for example, polynucleotides, are exemplary anionic bioactive agents.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination of the two. The DNA and RNA may optionally comprise unnatural nucleotides and may be single or double stranded. "Genetic material" refers also to sense and anti-sense DNA and RNA, that is, a nucleotide sequence which is complementary to a specific sequence of nucleotides in DNA and/or RNA.

"Pharmaceutical" or "drug" refers to any therapeutic or prophylactic agent which is used in the prevention, diagnosis, alleviation, treatment or cure of a malady, affliction, disease or injury in a patient. Therapeutically useful polynucleotides and polypeptides are included within the definition of drug.

"In combination with" refers to the incorporation of a bioactive agent with a cationic lipid compound of the present invention. The cationic lipid compound can be combined with the bioactive agent in any of a variety of different ways. For example, when the cationic lipid compound is in the form of a cationic vesicle or a cationic vesicular composition, the bioactive agent may be entrapped within the internal void of the vesicle. It is also contemplated that the bioactive agent may be integrated within the layer(s) or wall(s) of the vesicle, for example, by being interspersed among lipids which are contained within the vesicular layer(s) or wall(s). In addition, it is contemplated that the bioactive agent may be located on the surface of a vesicle. In this case, the bioactive agent may interact chemically with the surface of the vesicle and remain substantially adhered thereto. Such interaction may take the form of, for example, electrostatic interactions, hydrogen bonding, van der Waal's forces or covalent bonding. Alternatively, or in addition to, the bioactive agent may interact with the surface of the vesicle in a limited manner. Such limited interaction would permit migration of the bioactive agent, for example, from the surface of a first vesicle to the surface of a second vesicle.

"Intracellular" or "intracellularly" refers to the area within the plasma membrane of a cell, including the protoplasm, cytoplasm and/or nucleoplasm. "Intracellular delivery" refers to the delivery of a bioactive agent into the area within the plasma membrane of a cell.

"Cell" refers to any one of the minute protoplasmic masses which make up organized tissue, comprising a mass of protoplasm surrounded by a membrane, including nucleated and unnucleated cells and organelles.

"Immune competence" refers to the ability of the immune system to protect against pathogens or infectious agents.

The present invention is directed, in part, to a new class of cationic lipid compounds which are highly useful in connection with the intracellular delivery of one or more bioactive agents. The new class of lipids are described in more detail below.

Specifically, in one embodiment, the present invention relates to a cationic lipid compound of the formula

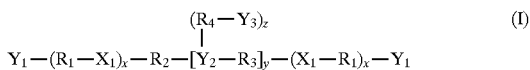

wherein:
each of x, y and z is independently an integer from 0 to about 100;
each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—;

each $X_2$ is independently O or S;

each $Y_1$ is independently a phosphate residue, $N(R_6)_a$—, $S(R_6)_a$—, $P(R_6)_a$— or —$CO_2R_6$, wherein a is an integer from 1 to 3;

each $Y_2$ is independently —$N(R_6)_b$—, —$S(R_6)_b$— or —$P(R_6)_b$—, wherein b is an integer from 0 to 2;

each $Y_3$ is independently a phosphate residue, $N(R_6)_a$—, $S(R_6)_a$—, $P(R_6)_a$— or —$CO_2R_6$, wherein a is an integer from 1 to 3;

each of $R_1$, $R_2$, $R_3$ and $R_4$ is independently alkylene of 1 to about 20 carbons;

each $R_5$ is independently hydrogen or alkyl of 1 to about 10 carbons; and each $R_6$ is independently —$[R_7$—$X_3]_c$—$R_8$ or —$R_9$—$[X_4$—$R_{10}]_d$—Q, wherein:

each of c and d is independently an integer from 0 to about 100;

each Q is independently a phosphate residue, —$N(R_{11})_q$, —$S(R_{11})_q$, —$P(R_{11})_q$ or —$CO_2R_{11}$, wherein q is an integer from 1 to 3;

each of $X_3$ and $X_4$ is independently —O—, —S—, —$NR_5$—, —C(=$X_2$)—, —C(=$X_2$)—$N(R_5)$—, —$N(R_5)$—C(=$X_2$)—, C(=$X_2$)—O—, —O—C(=$X_2$)— or —$X_2$—($R_5X_2$)P(=$X_2$)—$X_2$—;

each $R_7$ is independently alkylene of 1 to about 20 carbons;

each $R_8$ is independently hydrogen or alkyl of 1 to about 60 carbons;

each of $R_9$ and $R_{10}$ is independently alkylene of 1 to about 20 carbons; and each $R_{11}$ is independently —$[R_7$—$X_3]_c$—$R_8$ or —$R_9$—$[X_4$—$R_{10}]_d$—W, wherein:

each W is independently a phosphate residue, —$N(R_{12})_w$, —$S(R_{12})_w$, —$P(R_{12})_w$ or —$CO_2R_{12}$, wherein w is an integer from 1 to 3; and $R_{12}$ is —$[R_7$—$X_3]_c$—$R_8$; with the proviso that the compound of formula (I) comprises at least one, and preferably at least two, quaternary salts.

In the above formula (I), each of x, y and z is independently an integer from 0 to about 100. Preferably, each of x, y and z is independently an integer of from 0 to about 50, with integers from 0 to about 20 being more preferred. Even more preferably, each of x, y and z is independently an integer from 0 to about 10, with integers from 0 to about 5 being still more preferred. In certain particularly preferred embodiments, x is 1, y is 2 or 3 and z is 0 or 1.

In the above formula (I), each $X_1$ is independently —O—, —S—, —$NR_5$—, —C(=$X_2$)—, —C(=$X_2$)—$N(R_5)$—, —$N(R_5)$—C(=$X_2$)—, —C(=$X_2$)—O—, —O—C(=$X_2$)— or —$X_2$—($R_5X_2$)P(=$X_2$)—$X_2$—. Preferably, each $X_1$ is independently —C(=O)—$NR_5$—, —$NR_5$—C(=O)—, —C(=O)—O— or —O—C(=O)—.

Each $X_2$ in the definitions of $X_1$, $X_3$ and $X_4$ above is independently O or S. Preferably, $X_2$ is O.

In the above formula (I), each $Y_1$ is independently a phosphate residue, $N(R_6)_a$—, $S(R_6)_a$—, $P(R_6)_a$— or —$CO_2R_6$, wherein a is an integer from 1 to 3. Preferably, each $Y_1$ is independently a phosphate residue, $N(R_6)_a$— or —$CO_2R_6$, wherein a is 2 or 3. Preferably, a is 3.

Each $Y_2$ in formula (I) above is independently —$N(R_6)_b$—, —$S(R_6)_b$— or —$P(R_6)_b$—, wherein b is an integer from 0 to 2. Preferably, $Y_2$ is —$N(R_6)_b$—, wherein b is 1 or 2.

In the above formula (I), each $Y_3$ is independently a phosphate residue, $N(R_6)_a$—, $S(R_6)_a$—, $P(R_6)_a$— or —$CO_2R_6$, wherein a is an integer from 1 to 3. Preferably, each $Y_3$ is independently a phosphate residue, $N(R_6)_a$— or —$CO_2R_6$, wherein a is 2 or 3. Preferably, a is 3.

In the above formula (I), each of $R_1$, $R_2$, $R_3$ and $R_4$ is independently alkylene of 1 to about 20 carbons. Preferably, each of $R_1$, $R_2$, $R_3$ and $R_4$ is independently straight chain alkylene of 1 to about 10 carbons or cycloalkylene of about 4 to about 10 carbons. More preferably, each of $R_1$, $R_2$, $R_3$ and $R_4$ is independently straight chain alkylene of 1 to about 4 carbons or cycloalkylene of about 5 to about 7 carbons. Even more preferably, each of $R_1$, $R_2$, $R_3$ and $R_4$ is independently methylene, ethylene or cyclohexylene.

In the above definitions of $X_1$, $X_3$ and $X_4$, each $R_5$ is independently hydrogen or alkyl of 1 to about 10 carbons. Preferably, each $R_5$ is independently hydrogen or alkyl of 1 to about 4 carbons. More preferably, $R_5$ is hydrogen.

In the above definitions of $Y_1$, $Y_2$ and $Y_3$, each $R_6$ is independently —$[R_7$—$X_3]_c$—$R_8$ or —$R_9$—$[X_4$—$R_{10}]_d$—Q, wherein each of c and d is independently an integer from 0 to about 100. Preferably, each of c and d is independently an integer from 0 to about 50, with integers from 0 to about 20 being more preferred. Even more preferably, each of c and d is independently an integer from 0 to about 10, with integers from 0 to about 5 being still more preferred. In certain particularly preferred embodiments, c is 0 or 1 and d is 1.

Each Q in $R_6$ above is independently a phosphate residue, —$N(R_{11})_q$, —$S(R_{11})_q$, —$P(R_{11})_q$ or —$CO_2R_{11}$, wherein q is an integer from 1 to 3. Preferably, each Q is independently a phosphate residue, —$N(R_{11})_q$ or —$CO_2R_{11}$, wherein q is 2 or 3. Preferably, q is 3.

Also in the above definition of $R_6$, each of $X_3$ and $X_4$ is independently —O—, —S—, —$NR_5$—, —C(=$X_2$)—, —C(=$X_2$)—$N(R_5)$—, —$N(R_5)$—C(=$X_2$)—, —C(=$X_2$)—O—, —O—C(=$X_2$)— or —$X_2$—($R_5X_2$)P(=$X_2$)—$X_2$—, wherein each of $X_2$ and $R_5$ is independently as previously described. Preferably, each of $X_3$ and $X_4$ is independently —C(=O)—$NR_6$—, —$NR_5$—C(=O)—, —C(=O)—O— or —O—C(=O)—.

In the definitions of $R_6$, $R_{11}$ and $R_{12}$ above, each $R_7$ is independently alkylene of 1 to about 20 carbons. Preferably, each $R_7$ is independently alkylene of 1 to about 10 carbons, with alkylene of 1 to about 4 carbons being preferred. More preferably, each $R_7$ is independently methylene or ethylene.

Also in the definitions of $R_6$, $R_{11}$ and $R_{12}$ above, each $R_8$ is independently hydrogen or alkyl of 1 to about 60 carbons. Preferably, each $R_8$ is independently hydrogen or alkyl of 1 to about 40 carbons, with hydrogen or alkyl of 1 to about 20 carbons being more preferred. Even more preferred, each $R_8$ is independently hydrogen or alkyl of 1 to about 16 carbons. In certain particularly preferred embodiments, each $R_8$ is independently hydrogen, methyl, dodecyl or hexadecyl.

Each of $R_9$ and $R_{10}$ in the definitions of $R_6$ and $R_{11}$ above is independently alkylene of 1 to about 20 carbons. Preferably, each of $R_9$ and $R_{10}$ is independently alkylene of 1 to about 10 carbons. More preferably, each of $R_9$ and $R_{10}$ is independently alkylene of 1 to about 4 carbons. Even more preferably, each of $R_9$ and $R_{10}$ is independently methylene or ethylene.

Each $R_{11}$ in Q above is independently —$[R_7$—$X_3]_c$—$R_8$ or —$R_9$—$[X_4$—$R_{10}]_d$—W, wherein each of c, d, $X_3$, $X_4$, $R_7$, $R_8$, $R_9$ and $R_{10}$ is independently as previously described.

Each W in $R_{11}$ above is independently a phosphate residue, —$N(R_{12})_w$, —$S(R_{12})_w$, —$P(R_{12})_w$ or —$CO_2R_{12}$, wherein w is an integer from 1 to 3. Preferably, W is a phosphate residue, —$N(R_{12})_w$ or —$CO_2R_{12}$, wherein w is 2 or 3. Preferably, w is 3.

In the above definition of W, $R_{12}$ is —$[R_7$—$X_3]_c$—$R_8$, wherein each of c, $X_3$, $R_7$ and $R_8$ is independently as previously described.

In another embodiment of the present invention, there is provided a cationic lipid compound of the formula $$Y_1-R_1-Y_1 \quad (II)$$

wherein:
    each $Y_1$ is independently a phosphate residue, $N(R_2)_a-$, $S(R_2)_a-$, $P(R_2)_a-$ or $-CO_2R_2$, wherein a is an integer from 1 to 3;
    $R_1$ is alkylene of 1 to about 60 carbons containing 0 to about 30 $-O-$, $-S-$, $-NR_3-$ or $-X_2-(R_3X_2)P(=X_2)-X_2-$ heteroatoms or heteroatom groups;
    $R_2$ is a residue of the formula $-R_4-[(X_1-R_5)_x-Y_2]_y-R_6$, wherein:
        each of x and y is independently an integer from 0 to about 100;
        each $X_1$ is independently a direct bond, $-O-$, $-S-$, $-NR_3-$, $-C(=X_2)-$, $-C(=X_2)-N(R_3)-$, $-N(R_3)-C(=X_2)-$, $-C(=X_2)-O-$, $-O-C(=X_2)-$ or $-X_2-(R_3X_2)P(=X_2)-X_2-$;
        each $X_2$ is independently O or S;
        each $Y_2$ is independently $-S(R_2)_b-$, $-N(R_2)_b-$ or $-P(R_2)_b-$, wherein b is an integer from 0 to 2;
        each $R_3$ is independently hydrogen or alkyl of 1 to about 10 carbons;
        each of $R_4$ and $R_5$ is independently a direct bond or alkylene of 1 to about 30 carbons containing 0 to about 15 $-O-$, $-S-$, $-NR_3-$ or $-X_2-(R_3X_2)P(=X_2)-X_2-$ heteroatoms or heteroatom groups; and
        each $R_6$ is independently hydrogen or alkyl of 1 to about 60 carbons containing 0 to about 30 $-O-$, $-S-$, $-NR_3-$ or $-X_2-(R_3X_2)P(=X_2)-X_2-$ heteroatoms or heteroatom groups; with the proviso that the compound of formula (II) comprises at least one, and preferably at least two, quaternary salts.

In the above formula (II), each $Y_1$ is independently a phosphate residue, $N(R_2)_a-$, $S(R_2)_a-$, $P(R_2)_a-$ or $-CO_2R_2$, wherein a is an integer from 1 to 3. Preferably, each $Y_1$ is independently a phosphate residue, $-N(R_2)_a-$ or $-CO_2R_2$, wherein a is 2 or 3. Preferably, a is 3.

Also in the above formula (II), $R_1$ is alkylene of 1 to about 60 carbons containing 0 to about 30 $-O-$, $-S-$, $-NR_3-$ or $-X_2-(R_3X_2)P(=X_2)-X_2-$ heteroatoms or heteroatom groups. Preferably, $R_1$ is alkylene of 1 to about 40 carbons, with alkylene of 1 to about 20 carbons being preferred. More preferably, $R_1$ is straight chain alkylene of 1 to about 10 carbons or cycloalkylene of about 4 to about 10 carbons. Even more preferably, $R_1$ is straight chain alkylene of 1 to about 4 carbons or cycloalkylene of about 5 to about 7 carbons.

In the above definition of $Y_1$, $R_2$ is a residue of the formula $-R_4-[(X_1-R_5)_x-Y_2]_y-R_6$, wherein each of x and y is independently an integer from 0 to about 100. Preferably, each of x and y is independently an integer from 0 to about 50, with integers from 0 to about 20 being more preferred. Even more preferably, each of x and y is independently an integer from 0 to about 10.

In the above definition of $R_2$, each $X_1$ is independently a direct bond, $-O-$, $-S-$, $-NR_3-$, $-C(=X_2)-$, $-C(=X_2)-N(R_3)-$, $-N(R_3)-C(=X_2)-$, $-C(=X_2)-O-$, $-O-C(=X_2)-$ or $-X_2-(R_3X_2)P(=X_2)-X_2-$. Preferably, $X_1$ is a direct bond, $-C(=X_2)-N(R_3)-$, $-N(R_3)-C(=X_2)-$, $-C(=X_2)-O-$ or $-O-C(=X_2)-$.

Each $X_2$ in the above definitions of $X_1$, $R_1$, $R_4$, $R_5$ and $R_6$ is independently O or S. Preferably, $X_2$ is O.

Each $Y_2$ in the above definition of $R_2$ is independently $-S(R_2)_b-$, $-N(R_2)_b-$ or $-P(R_2)_b-$, wherein b is an integer of from 0 to 2. Preferably, $Y_2$ is $-N(R_2)_b-$ and b is 1 or 2.

In the above definitions of $X_1$, $R_1$, $R_4$, $R_5$ and $R_6$, each $R_3$ is independently hydrogen or alkyl of 1 to about 10 carbons. Preferably, each $R_3$ is independently hydrogen or alkyl of 1 to about 4 carbons. More preferably, $R_3$ is hydrogen.

In the above definition of $R_2$, each of $R_4$ and $R_5$ is independently a direct bond or alkylene of 1 to about 30 carbons containing 0 to about 15 $-O-$, $-S-$, $-NR_3-$ or $-X_2-(R_3X_2)P(=X_2)-X_2-$ heteroatoms or heteroatom groups. Preferably, each of $R_4$ and $R_5$ is independently a direct bond or alkylene of 1 to about 20 carbons. More preferably, each of $R_4$ and $R_5$ is independently a direct bond, straight chain alkylene of 1 to about 10 carbons or cycloalkylene of 4 to about 10 carbons. Even more preferably, each of $R_4$ and $R_5$ is independently a direct bond, straight chain alkylene of 1 to about 4 carbons or cycloalkylene of about 5 to about 7 carbons.

Each $R_6$ in $R_2$ above is independently hydrogen or alkyl of 1 to about 60 carbons containing 0 to about 30 $-O-$, $-S-$, $-NR_3-$ or $-X_2-(R_3X_2)P(=X_2)-X_2-$ heteroatoms or heteroatom groups. Preferably, each $R_6$ is independently hydrogen or alkyl of 1 to about 40 carbons. More preferably, each $R_6$ is independently hydrogen or alkyl of 1 to about 20 carbons.

In yet another embodiment of the present invention, there is provided a cationic lipid compound of the formula

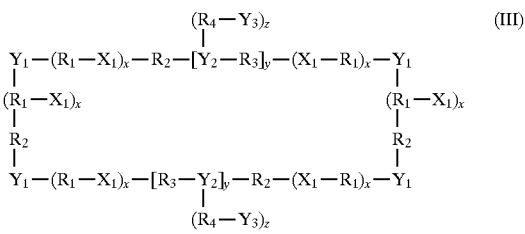

wherein:
    each of x, y and z is independently an integer from 0 to about 100;
    each $X_1$ is independently $-O-$, $-S-$, $-NR_5-$, $-C(=X_2)-$, $-C(=X_2)-N(R_5)-$, $-N(R_5)-C(=X_2)-$, $-C(=X_2)-O-$, $-O-C(=X_2)-$ or $-X_2-(R_5X_2)P(=X_2)-X_2-$;
    each $X_2$ is independently O or S;
    each $Y_1$ is independently $-O-$, $-N(R_6)_a-$, $-S(R_6)_a-$ or $-P(R_6)_a-$, wherein a is an integer from 0 to 2;
    each $Y_2$ is independently $-N(R_6)_a-$, $-S(R_6)_a-$ or $-P(R_6)_a-$, wherein a is an integer from 0 to 2;
    each $Y_3$ is independently a phosphate residue, $N(R_6)_b-$, $S(R_6)_b-$, $P(R_6)_b-$ or $-CO_2R_6$, wherein b is an integer from 1 to 3;
    each of $R_1$, $R_2$, $R_3$ and $R_4$ is independently alkylene of 1 to about 20 carbons;
    each $R_5$ is independently hydrogen or alkyl of 1 to about 10 carbons; and
    each $R_6$ is independently $-[R_7-X_3]_c-R_8$ or $-R_9-[X_4-R_1]_d-Q$, wherein:
        each of c and d is independently an integer from 0 to about 100;
        each Q is independently a phosphate residue, $-N(R_{11})_q$, $-S(R_{11})_q$, $-P(R_{11})_q$ or $-CO_2R_{11}$, wherein q is an integer from 1 to 3;

each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—;

each $R_7$ is independently alkylene of 1 to about 20 carbons;

each $R_8$ is independently hydrogen or alkyl of 1 to about 60 carbons;

each of $R_9$ and $R_{10}$ is independently alkylene of 1 to about 20 carbons; and each $R_{11}$ is independently —[$R_7$—$X_3$]$_c$—$R_8$ or —$R_9$—[$X_4$—$R_{10}$]$_d$—W, wherein:

each W is independently a phosphate residue, —N($R_{12}$)$_w$, —S($R_{12}$)$_w$, —P($R_{12}$)$_w$ or —$CO_2R_{12}$, wherein w is an integer from 1 to 3; and $R_{12}$ is —[$R_7$—$X_3$]$_c$—$R_8$; with the proviso that the compound of formula (III) comprises at least one, and preferably at least two, quaternary salts.

In the above formula (III), each of x, y and z is independently an integer from 0 to about 100. Preferably, each of x, y and z is independently an integer from 0 to about 50, with integers from 0 to about 20 being more preferred. Even more preferably, each of x, y and z is independently an integer from 0 to about 10. Still more preferably, each of x, y and z is independently an integer from 0 to about 5. In certain particularly preferred embodiments, x is 1, y is 2 or 3 and z is 0 or 1.

In the above formula (III), each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—. Preferably, each $X_1$ is independently —C(=O)—$NR_5$—, —$NR_5$—C(=O)—, —C(=O)—O— or —O—C(=O)—.

In the above definitions of $X_1$, $X_3$ and $X_4$, each $X_2$ is independently O or S. Preferably, $X_2$ is O.

Each $Y_1$ in formula (III) above is independently —O—, —N($R_6$)$_a$—, —S($R_6$)$_a$— or —P($R_6$)$_a$—, wherein a is an integer from 0 to 2. Preferably, $Y_1$ is —N($R_6$)$_a$—, wherein a is 1 or 2.

Each $Y_2$ in formula (III) above is independently —N($R_6$)$_a$—, —S($R_6$)$_a$— or —P($R_6$)$_a$—, wherein a is an integer from 0 to 2. Preferably, $Y_2$ is —N($R_6$)$_a$—.

In the above formula (III), each $Y_3$ is independently a phosphate residue, N($R_6$)$_b$—, S($R_6$)$_b$—, P($R_6$)$_b$— or —$CO_2R_6$, wherein b is an integer from 1 to 3. Preferably, each $Y_3$ is independently a phosphate residue or N($R_6$)$_b$—, wherein b is 2 or 3. Preferably, b is 3.

In the above formula (III), each of $R_1$, $R_2$, $R_3$ and $R_4$ is independently alkylene of 1 to about 20 carbons. Preferably, each of $R_1$, $R_2$, $R_3$ and $R_4$ is independently straight chain alkylene of 1 to about 10 carbons or cycloalkylene of about 4 to about 10 carbons. More preferably, each of $R_1$, $R_2$, $R_3$ and $R_4$ is independently straight chain alkylene of 1 to about 4 carbons or cycloalkylene of about 5 to about 7 carbons. Even more preferably, each of $R_1$, $R_2$, $R_3$ and $R_4$ is independently methylene, ethylene or cyclohexylene.

In the above definitions of $X_1$, $X_3$ and $X_4$, each $R_5$ is independently hydrogen or alkyl of 1 to about 10 carbons. Preferably, each $R_5$ is independently hydrogen or alkyl of 1 to about 4 carbons. More preferably, $R_5$ is hydrogen.

In the above definitions of $Y_1$, $Y_2$ and $Y_3$, each $R_6$ is independently —[$R_7$—$X_3$]$_c$—$R_8$ or —$R_9$—[$X_4$—$R_{10}$]$_d$—Q, wherein each of c and d is independently an integer from 0 to about 100. Preferably, each of c and d is independently an integer from 0 to about 50, with integers from 0 to about 20 being more preferred. Even more preferably, each of c and d is independently an integer from 0 to about 10, with integers from 0 to about 5 being still more preferred. In certain particularly preferred embodiments, c is 0 or 1 and d is 1.

Each Q in $R_6$ above is independently a phosphate residue, —N($R_{11}$)$_q$, —S($R_{11}$)$_q$, —P($R_{11}$)$_q$ or —$CO_2R_{11}$, wherein q is an integer from 1 to 3. Preferably, each Q is independently a phosphate residue, —N($R_{11}$)$_q$ or —$CO_2R_{11}$, wherein q is 2 or 3. Preferably, q is 3.

Also in the above definition of $R_6$, each of $X_3$ and $X_4$ is independently —O—, —S—, —$NR_5$—, —C(=$X_2$)—, —C(=$X_2$)—N($R_5$)—, —N($R_5$)—C(=$X_2$), —C(=$X_2$)—O—, —O—C(=$X_2$)— or —$X_2$—($R,X_2$)P(=$X_2$)—$X_2$—, wherein $X_2$ and $R_5$ are as previously described. Preferably, each of $X_3$ and $X_4$ is independently —C(=O)—$NR_5$—, —$NR_5$—C(=O)—, —C(=O)—O— or —O—C(=O)—.

In the definitions of $R_6$, $R_{11}$ and $R_{12}$ above, each $R_7$ is independently alkylene of 1 to about 20 carbons. Preferably, each $R_7$ is independently alkylene of 1 to about 10 carbons, with alkylene of 1 to about 4 carbons being preferred. More preferably, each $R_7$ is independently methylene or ethylene.

Also in the definitions of $R_6$, $R_{11}$ and $R_{12}$ above, each $R_8$ is independently hydrogen or alkyl of 1 to about 60 carbons. Preferably, each $R_8$ is independently hydrogen or alkyl of 1 to about 40 carbons, with hydrogen or alkyl of 1 to about 20 carbons being more preferred. In certain particularly preferred embodiments, each $R_8$ is independently hydrogen, methyl, dodecyl or hexadecyl.

Each of $R_9$ and $R_{10}$ in the definitions of $R_6$ and $R_{11}$ above is independently alkylene of 1 to about 20 carbons. Preferably, each of $R_9$ and $R_{10}$ is independently alkylene of 1 to about 10 carbons. More preferably, each of $R_9$ and $R_{10}$ is independently alkylene of 1 to about 4 carbons. Even more preferably, each of $R_9$ and $R_{10}$ is independently methylene or ethylene.

In Q above, each $R_{11}$ is independently —[$R_7$—$X_3$]$_c$—$R_8$ or —$R_9$—[$X_4$—$R_{10}$]$_d$—W, wherein each of c, d, $X_3$, $X_4$, $R_7$, $R_8$, $R_9$ and $R_{10}$ is independently as previously described.

Each W in $R_{11}$ above is independently a phosphate residue, —N($R_{12}$)$_w$, —S($R_{12}$)$_w$, —P($R_{12}$)$_w$ or —$CO_2R_{12}$, wherein w is an integer from 1 to 3. Preferably, each W is independently a phosphate residue, —N($R_{12}$)$_w$ or —$CO_2R_{12}$, wherein w is 2 or 3. Preferably, w is 3.

In W above, $R_{12}$ is —[$R_7$—$X_3$]$_c$—$R_8$, wherein each of c, $X_3$, $R_7$ and $R_8$ is independently as previously described.

In the above formulas, it is intended that when any symbol appears more than once in a particular formula or substituent, its meaning in each instance is independent of the other.

Also in the above formulas, it is intended that when each of two or more adjacent symbols is defined as being "a direct bond" to provide multiple, adjacent direct bonds, the multiple and adjacent direct bonds devolve into a single direct bond.

The compounds of formulas (I), (II) and (III) above are exemplary of the cationic lipid compounds which are the subject of the present invention. The cationic or positively charged properties of the cationic lipid compounds is due to the presence of at least one cationic group. In preferred embodiments, at least two cationic groups are present in the cationic lipid compounds of the present invention. The existence of the cationic groups imparts desirable and beneficial properties to the cationic lipid compounds, such properties being absent from lipid compounds known heretofore. In particular, the cationic lipid compounds of the present invention possess improved ability to bind and/or chelate with bioactive agents relative to lipid compounds of the prior art. This binding and/or chelation of the present cationic lipid compounds with bioactive agents is referred to generally hereinafter as "interaction". Accordingly, the cationic lipid compounds of the present invention are particularly suitable for use as carriers for bioactive agents and for the intracellular delivery of bioactive agents.

While the inventors do not wish to be bound by any theory or theories of operation, it is believed that the improved ability of the cationic lipid compounds of the present invention to interact with bioactive agents is due, at least in part, to the enhanced charge densities of the present lipid compounds. In this connection, the present cationic lipid compounds possess an increased, positive charge density due to the existence of at least one, and preferably at least two, cationic groups. As discussed in detail below, this enhanced charge density results in unexpectedly desirable interaction with bioactive agents.

Bioactive agents, whether neutral (uncharged) or positively or negatively charged, typically contain a dipole moment and/or one or more heteroatoms, for example, nitrogen, oxygen and sulfur atoms. These heteroatoms generally possess one or more unshared pairs of electrons. It is believed that the positively charged lipid compounds of the present invention electrostatically interact with the negatively charged region of the dipole moment and/or with the unshared pair(s) of electrons on the heteroatoms.

The cationic lipid compounds of the present invention possess particularly improved abilities to interact with bioactive agents which are anionic and which contain one or more anionic groups. Such anionic bioactive agents possess a greater negative charge density relative to neutral or positively charged bioactive agents.

Due to the improved ability of the cationic lipid compounds of the present invention to interact with bioactive agents, the present lipid compounds are particularly suitable for use as carriers for the intracellular delivery of bioactive agents. Thus, the cationic lipid compounds of the present invention are particularly applicable for use in vitro and/or in vivo in methods for the treatment of diseases, including genetic diseases, which involve or require the intracellular delivery of bioactive agents.

As discussed in detail below, the cationic lipid compounds are also particularly suitable for use in the formulation of cationic vesicles, including micelles and liposomes. The inventors have found that cationic liposomes are also particularly suitable for use as carriers for the intracellular delivery of bioactive agents.

As noted above, the cationic lipid compounds of the present invention comprise at least one, and preferably at least two, cationic groups. In an alternate embodiment, the cationic lipid compounds comprise more than at least two cationic groups, for example, at least three cationic groups. In another alternate embodiment, the cationic lipid compounds comprise at least four cationic groups. In yet another alternate embodiment, the cationic lipid compounds comprise at least five cationic groups. In certain embodiments, the cationic lipid compounds comprise more than five cationic groups.

For purposes of illustration only, and not for purposes of limitation, cationic groups may be provided, for example, in the compounds of formula (I) by the group $Y_1$. Thus, for example, when $Y_1$ in formula (I) is $N(R_6)_a$— and a is 3, a quaternary salt is formed in that the nitrogen atom of $Y_1$ is bonded to four other carbon atoms. The nitrogen atom is therefore positively charged.

Other cationic groups, in addition to the cationic groups discussed above, would be apparent to one of ordinary skill in the art based on the present disclosure.

In embodiments in which the cationic group comprises a quaternary salt, the cationic lipid compound is generally, although not necessarily, associated with a counter ion. Preferably, the counter ion is a pharmaceutically-acceptable counter ion.

In certain preferred embodiments of the present invention, the counter ion is selected from the group consisting of halide, $R_{13}SO_3^-$, $R_{13}CO_2^-$, phosphate, sulfite, nitrate, gluconate, guluronate, galacturonate, estolate and mesylate, wherein $R_{13}$ is hydrogen, alkyl of 1 to about 20 carbons or aryl of about 6 to about 10 carbons. Preferably, $R_{13}$ is hydrogen or alkyl of 1 to about 10 carbons or phenyl. In other preferred embodiments, the counter ion is halide (fluoride, chloride, bromide or iodide), with iodide being preferred. Various other counter ions, including pharmaceutically acceptable counter ions, would be apparent to one skilled in the art based on the present disclosure.

As those skilled in the art will recognize, once placed in possession of the present invention, cationic lipid compositions may be readily formulated from the cationic lipid compounds. Depending on the desired physical properties, cationic lipid compositions may be prepared from the cationic lipid compounds, alone or in combination with other materials, for example, materials which act to stabilize the composition.

It is generally desirable to combine the cationic lipid compounds with other materials, including stabilizing materials, for example, additional amphipathic compounds, to stabilize and/or otherwise improve the properties of the compositions. Compositions which are prepared from the present cationic lipid compounds and additional amphipathic compounds include, for example, suspensions, emulsions, vesicles and hexagonal H II phase structures.

A wide variety of materials which act to stabilize the compositions of the present invention are readily available and would be apparent to a person skilled in the art based on the present disclosure. Included among such materials are additional amphipathic compounds, such as lipids, and fatty materials. The particular stabilizing material which is ultimately combined with the present cationic lipid compounds may be selected as desired to optimize the properties of the resulting composition. It is believed that suitable stabilizing materials are readily identifiable and that compositions of the present cationic lipid compounds can be prepared by one skilled in the art without undue experimentation.

It is also desirable, in certain instances, to combine the cationic lipid compounds with a material which is capable of promoting fusion of the lipid with the cell membrane. Such materials enhance the ability of the cationic lipid compositions to deliver intracellularly the bioactive agent. Certain of such materials are capable also of promoting gene expression. These latter materials are particularly suitable for use in the transfection of genetic material. Examples of materials which are capable of promoting fusion of the cationic lipid composition with cell membranes include, for example, ammonium sulfate, cytochalasin B, chloroquine, glycerol, propylene glycol and poly(ethylene glycol).

In one embodiment of the invention, a cationic lipid composition is provided which comprises a cationic lipid suspension and/or emulsion. Lipid suspensions and emulsions are well known and may be prepared using conventional techniques. As those skilled in the art will recognize, a suspension is a mixture of finely divided particles floating in a liquid, and an emulsion is a colloidal mixture of two or more liquids. The components of the suspension/emulsion are generally mixed together by mechanical agitation, optionally but preferably in the presence of small amounts of additional substances known as emulsifiers.

Typically, in preparing the suspension/emulsion, the cationic lipid compounds may be added to ethanol or chloroform or any other suitable organic solvent and agitated by hand or by using mechanical techniques. The solvent is then evaporated from the mixture leaving a dried glaze of cationic lipid. The lipids are resuspended in aqueous media, such as phosphate buffered saline, resulting in a suspension/emulsion. To achieve a more homogeneous size distribution of the involved lipids, the mixture may be sonicated using conventional sonication techniques as well as microfluidization (using, for example, a MICROFLUIDIZER™, Newton, Mass.), and/or high pressure extrusion (such as, for example, 600 psi) using an Extruder Device (Lipex Biomembranes, Vancouver, Canada). The lipid may be also subjected to one or more alternating cycles of freezing and thawing to promote the formation of a substantially uniform suspension/emulsion. In addition, a salt, for example, sodium chloride, is optionally added to the suspension/emulsion in a concentration of about 0.05 molar (M) to about 1.0M to promote the formation of substantially uniform dispersions. Bioactive agents may be added to the cationic lipid compounds during the preparation of the suspension/emulsion, such as at the stage where the lipids are added to the organic solvent or at other stages of preparation, or may be added after the cationic lipid suspension/emulsion has been formed, as desired. In preparing the suspensions/emulsions, particularly useful additives are, for example, soybean lecithin, glucose, Pluronic F-68, and D,L-α-tocopherol (Vitamin E), generally in an amount of about 0.03 to about 5 percent by weight. These additives are particularly useful where intravenous applications are desired. Techniques and ingredients for formulating lipid suspensions/emulsions are well known in the art and are applicable to the present cationic suspensions/emulsions. Suitable procedures and suspension/emulsion ingredients are reported, for example, in *Modern Pharmaceutics*, pp. 505–507, Gilbert Baker and Christopher Rhodes, eds., Marcel Dekker Inc., New York, N.Y. (1990), the disclosures of which are hereby incorporated herein by reference in its entirety.

In another embodiment of the invention, a cationic lipid composition is provided which comprises a cationic vesicular composition. The cationic vesicular composition may comprise micelles and/or liposomes. With particular reference to cationic micelle compositions, the following discussion is provided.

Micelles may be prepared using any one of a variety of conventional micellar preparatory methods which will be apparent to those skilled in the art. These methods typically involve suspension of the cationic lipid compound in an organic solvent, evaporation of the solvent, resuspension in an aqueous medium, sonication and centrifugation. The foregoing methods, as well as others, are discussed, for example, in Canfield et al., *Methods in Enzymology*, Vol. 189, pp. 418–422 (1990); El-Gorab et al, *Biochem. Biophys. Acta*, Vol. 306, pp. 58–66 (1973); *Colloidal Surfactant*, Shinoda, K., Nakagana, Tamamushi and Isejura, Academic Press, NY (1963) (especially "The Formation of Micelles", Shinoda, Chapter 1, pp. 1–88); *Catalysis in Micellar and Macro molecular Systems*, Fendler and Fendler, Academic Press, NY (1975). The disclosures of each of the foregoing publications are incorporated by reference herein, in their entirety. The micelles may be prepared in the presence of a bioactive agent or the bioactive agent may be added to pre-formed micelles.

It is generally desirable to include one or more stabilizing materials in the micellar compositions. Exemplary materials which may be combined with the cationic lipid compounds to stabilize the micellar compositions produced therefrom include lauryltrimethylammonium bromide, cetyltrimethylammonium bromide, myristyl trimethylammonium bromide, alkyldimethylbenzylammonium chloride, wherein the alkyl group is about 12 to about 16 carbons, benzyldimethyldodecylammonium bromide or chloride, benzyldimethylhexadecylammonium bromide or chloride, benzyldimethyltetradecylammonium bromide or chloride, cetyldimethylethylammonium bromide or chloride, cetylpyridinium bromide and chloride and lauryl sulfate.

Other materials for stabilizing the micellar compositions, in addition to those exemplified above, would be apparent to one skilled in the art based on the present disclosure.

As noted above, the cationic vesicular composition may comprise cationic liposomes. Cationic liposomes are particularly effective as carriers for the intracellular delivery of bioactive agents and are therefore preferred cationic lipid compositions. The present cationic liposomes are highly stable and permit substantially complete entrapment of a bioactive agent within the vesicle. Thus, compositions which comprise cationic liposomes are highly effective carriers for the transfection of bioactive agents in that the liposomes are capable of (A) effectively interacting with the bioactive agent by virtue of electrostatic forces (as discussed above in connection with the cationic lipid compounds, generally); and (B) entrapping the bioactive agent within the liposome vesicle. The cationic liposomes are also highly biocompatible.

The cationic liposome compositions may comprise one or more cationic lipid compounds. In any given liposome, the cationic lipid compound(s) may be in the form of a monolayer or bilayer, and the mono- or bilayer lipids may be used to form one or more mono- or bilayers. In the case of more than one mono- or bilayer, the mono- or bilayers are generally concentric. Thus, the lipids may be used to form a unilamellar liposome (comprised of one monolayer or bilayer), an oligolamellar liposome (comprised of two or three monolayers or bilayers) or a multilamellar liposome (comprised of more than three monolayers or bilayers).

As with the suspensions/emulsions and micelles above, cationic liposome compositions are preferably formulated from both the present cationic lipid compounds and additional stabilizing materials, including additional amphipathic compounds. In the case of liposomes, the additional amphipathic compounds preferably comprise lipids. A wide variety of additional lipids are available which may be incorporated into the liposome compositions. Preferably, the lipids are selected to optimize certain desirable properties of the liposomes, including serum stability and plasma half-life. The selection of suitable lipids in the preparation of cationic liposome compositions would be apparent to a person skilled in the art and can be achieved without undue experimentation, based on the present disclosure.

Lipids which may be used in combination with the resent cationic lipid compounds and in the formulation of cationic liposome compositions include ZONYL™ fluoro surfactants (DuPont Chemicals, Wilmington, Del.) and the fluorine-containing compounds which are described in the following publications: S. Gaentzler et al., *New Journal of Chemistry*, Vol. 17(5), pp. 337–344 (1993); C. Santaella et al., *New Journal of Chemistry*, Vol. 16(3), pp. 399–404 (1992); and L. sole-Violan, *New Journal of Chemistry*, Vol. 17(8,9), pp. 581–583 (1993); the disclosures of each of which are hereby incorporated by reference, in their entireties. Other exemplary lipids which may be used in the preparation of cationic liposome compositions include phosphatidylcholine with both saturated and unsaturated lipids, including dioleoylphosphatidylcholine, dimyristoylphosphatidylcholine, dipalmitoylphosphatidylcholine (DPPC) and distearoylphosphatidylcholine; phosphatidylethanolamines, such as dioleoylphosphatidylethanolamine and dipalmitoylphosphatidylethanolamine (DPPE); phosphatidylserine; phosphatidylglycerol; sphingolipids; sphingomyelin; lysolipids; glycolipids, such as ganglioside GM1; glucolipids; sulfatides; glycosphingolipids; phosphatidic acids, such as dipalmitoylphosphatidic acid (DPPA); palmitic acid; stearic acid; arachidonic acid; oleic acid; fatty acids; lipids with ether and ester-linked fatty acids; polymerizable lipids; cholesterol, cholesterol sulfate and cholesterol hemisuccinate; 12-{[(7'-diethylaminocoumarin-3-yl)carbonyl]methylamino}octadecanoic acid; N-[12-{[(7'-diethylaminocoumarin-3-yl)carbonyl]methylamino}-octadecanoyl]-2-aminopalmitic acid; cholesteryl-4'-trimethylaminobutanoate; N-succinyldioleoylphosphatidyl-ethanolamine; 1,2-dioleoyl-sn-glycerol; 1,2-dipalmitoyl-sn-3-succinylglycerol; 1,3-dipalmitoyl-2-succinyl-glycerol; 1-hexadecyl-2-palmitoylglycerophosphatidylethanolamine; and palmitoylhomocysteine.

Lipids bearing polymers, including the hydrophilic polymers poly(ethylene glycol) (PEG), polyvinylpyrrolidone, and poly(vinyl alcohol), may also be included in the liposome compositions of the present invention. Examples of suitable hydrophilic polymers include, for example, PEG 2,000, PEG 5,000 and PEG 8,000, which have molecular weights of 2,000, 5,000 and 8,000, respectively. Other suitable polymers, hydrophilic and otherwise, will be readily apparent to those skilled in the art based on the present disclosure. Polymers which may be incorporated via alkylation or acylation reactions onto the surface of the liposome are particularly useful for improving the stability and size distribution of the liposomes. Exemplary lipids which bear hydrophilic polymers include, for example, dipalmitoylphosphatidylethanolamine-PEG, dioleoylphosphatidylethanolamine-PEG and distearylphosphatidyl-ethanolamine-PEG.

Other materials for use in the preparation of cationic liposome compositions, in addition to those exemplified above, would be apparent to one skilled in the art based on the present disclosure.

The amount of stabilizing material, such as, for example, additional amphipathic compound, which is combined with the present cationic lipid compounds may vary depending upon a variety of factors, including the specific cationic lipid compound(s) of the invention selected, the specific stabilizing material(s) selected, the particular use for which it is being employed, the mode of delivery, and the like. The amount of stabilizing material to be combined with the present cationic lipid compounds in a particular situation, and the ratio of stabilizing material to cationic lipid compound, will vary and is readily determinable by one skilled in the art based on the present disclosure. In general, for example, it has been found that higher ratios, that is, ratios higher than about 4:1, 3:1 or 2:1, of cationic lipid compound to stabilizing lipid, are preferred.

A wide variety of methods are available in connection with the preparation of cationic liposome compositions. Accordingly, the cationic liposomes may be prepared using any one of a variety of conventional liposome preparatory techniques which will be apparent to those skilled in the art. These techniques include solvent dialysis, French press, extrusion (with or without freeze thaw), reverse phase evaporation, microemulsification and simple freeze-thawing. The liposomes may also be prepared by various processes which involve shaking or vortexing. This may be achieved, for example, by the use of a mechanical shaking device, such as a WIG-L-BUG™ (Crescent Dental, Lyons, Ill.). Conventional microemulsification quipment, such as a MICROFLUIDIZER™ (Microfluidics, Woburn, Mass.) may be used also.

Additional methods for the preparation of liposome ompositions from the cationic lipid compounds of the resent invention include, for example, sonication, chelate dialysis, homogenization, solvent infusion, spontaneous formation, solvent vaporization, controlled detergent dialysis, and others, each involving the preparation of liposomes in various fashions. Methods which involve freeze-thaw techniques are preferred in connection with the preparation of liposomes from the cationic lipid compounds of the present invention. Suitable freeze-thaw techniques are described, for example, in copending U.S. application Ser. No. 07/838,504 now abandoned, filed Feb. 19, 1992, the disclosures of which are incorporated herein by reference in their entirety. Preparation of the liposomes may be carried out in a solution, such as an aqueous saline solution, aqueous phosphate buffer solution, or sterile water, containing one or more bioactive agents, so that the bioactive agent is encapsulated in the liposome or incorporated into the liposome membrane. Alternatively, the bioactive agents may be added to previously formed liposomes.

The size of the liposomes can be adjusted, if desired, by a variety of techniques, including extrusion, filtration, sonication and homogenization. In addition, the size of the liposomes can be adjusted by the introduction of a laminar stream of a core of liquid into an immiscible sheath of liquid. Other methods for adjusting the size of the cationic liposomes and for modulating the resultant liposomal biodistribution and clearance of the liposomes would be apparent to one skilled in the art based on the present disclosure. Preferably, the size of the cationic liposomes is adjusted by extrusion under pressure through pores of a defined size. Although liposomes employed in the subject invention may be of any one of a variety of sizes, preferably the liposomes are small, that is, less than about 100 nanometer (nm) in outside diameter.

Many of the foregoing liposomal preparatory techniques, as well as others, are discussed, for example, in U.S. Pat. No. 4,728,578; U.K. Patent Application GB 2193095 A; U.S. Pat. No. 4,728,575; U.S. Pat. No. 4,737,323; International Application Serial No. PCT/US85/01161; Mayer et al., *Biochimica et Biophysica Acta*, Vol. 858, pp. 161–168 (1986); Hope et al., *Biochimica et Biophysica Acta*, Vol. 812, pp. 55–65 (1985); U.S. Pat. No. 4,533,254; Mayhew et al., *Methods in Enzymology*, Vol. 149, pp. 64–77 (1987); Mayhew et al., *Biochimica et Biophysica Acta*, Vol 755, pp. 169–74 (1984); Cheng et al, *Investigative Radiology*, Vol. 22, pp. 47–55 (1987); International Application Serial No. PCT/US89/05040; U.S. Pat. No. 4,162,282; U.S. Pat. No. 4,310,505; U.S. Pat. No. 4,921,706; and *Liposome Technology*, Gregoriadis, G., ed., Vol. I, pp. 29–31, 51–67 and 79–108 (CRC Press Inc., Boca Raton, Fla. 1984), the disclosures of each of which are hereby incorporated by reference herein, in their entirety.

Although any of a number of varying techniques can be used, the liposomes of the present invention are preferably prepared using a shaking technique. Preferably, the shaking techniques involve agitation with a mechanical shaking apparatus, such as a WIG-L-BUG™ (Crescent Dental, Lyons, Ill.), such as those disclosed in copending U.S. application Ser. No. 160,232, filed Nov. 30, 1993, (issued as U.S. Pat. No. 5,542,935), the disclosures of which are hereby incorporated herein by reference in their entirety.

As those skilled in the art will recognize, any of the cationic lipid compounds and compositions containing the cationic lipid compounds, with or without bioactive agents, may be lyophilized for storage, and reconstituted in, for example, an aqueous medium (such as sterile water or phosphate buffered solution, or aqueous saline solution), with the aid of vigorous agitation. To prevent agglutination or fusion of the lipids as a result of lyophilization, it may be useful to include additives which prevent such fusion or agglutination from occurring. Additives which may be useful include sorbitol, mannitol, sodium chloride, glucose, trehalose, polyvinylpyrrolidone and poly(ethylene glycol), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

The inventors have found that intracellular delivery of bioactive agents through the use of cationic lipid compositions, including suspensions/emulsions and vesicular compositions, may be enhanced by the presence of a gaseous substance. It is contemplated that the gaseous substance promotes uptake by cells of the bioactive agent. Thus, in certain preferred embodiments, a gas, such as an inert gas, is incorporated in the cationic lipid compositions. Alternatively, a precursor to a gaseous substance may be incorporated in the cationic lipid compositions. Such precursors include, for example, materials which are capable of converting in vivo to a gas, and preferably, to an inert gas.

Preferred gases are gases which are inert and which are biocompatible, that is, gases which are not injurious to biological function. Preferable gases include those selected from the group consisting of air, noble gases, such as helium, neon, argon and xenon, carbon dioxide, nitrogen, fluorine, oxygen, sulfur hexafluoride, fluorocarbons, perfluorocarbons, and mixtures thereof. Other gases, including the gases exemplified above, would be readily apparent to one skilled in the art based on the present disclosure.

In preferred embodiments, the gas comprises a perfluorocarbon. Preferably, the perfluorocarbon is selected from the group consisting of perfluoromethane, perfluoroethane, perfluoropropane, perfluorobutane, perfluorocyclobutane, and mixtures thereof. More preferably, the perfluorocarbon gas is perfluoropropane or perfluorobutane, with perfluoropropane being particularly preferred.

As noted above, it may also be desirable to incorporate in the cationic lipid compositions a precursor to a gaseous substance. Such precursors include materials that are capable of being converted in vivo to a gas. Preferably, the gaseous precursor is biocompatible, and the gas produced in vivo is biocompatible also.

Among the gaseous precursors which are suitable for use in the present compositions are pH sensitive agents. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid ($H_2CO_3$) is an example of a suitable inorganic acid, and aminomalonic acid is an example of a suitable organic acid. Other acids, including inorganic and organic acids, would be readily apparent to one skilled in the art based on the present disclosure.

Preferably, the gaseous precursor is a salt which is selected from the group consisting of an alkali metal salt, an ammonium salt and mixtures thereof. More preferably, the salt is selected from the group consisting of carbonate, bicarbonate, sesquecarbonate, aminomalonate and mixtures thereof.

Examples of gaseous precursor materials for use in the cationic lipid compositions of the present invention include lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, Vol. 9, no. 3, pp. 525–532 (1970); Fitzpatrick et al., *Inorganic Chemistry*, Vol. 13, no. 3 pp. 568–574 (1974); and Stelmashok et al., *Koordinatsionnaya Khimiya*, Vol. 3, no. 4, pp. 524–527 (1977). The disclosures of these publications are hereby incorporated herein by reference.

In addition to, or instead of, being sensitive to changes in pH, the gaseous precursor materials may also comprise compounds which are sensitive to changes in temperature. Such temperature sensitive agents include materials which have a boiling point of greater than about 37° C. Exemplary temperature sensitive agents are methyl lactate, perfluoropentane and perfluorohexane. The gaseous precursor materials may be also photoactivated materials, such as diazonium ion and aminomalonate. As discussed more fully hereinafter, certain lipid compositions, and particularly vesicular compositions, may be designed so that gas is formed at the target tissue or by the action of sound on the particle. Examples of gaseous precursors are described, for example, in U.S. Pat. Nos. 5,088,499 and 5,149,319. These patents are hereby incorporated herein by reference in their entirety. Other gaseous precursors, in addition to those exemplified above, will be apparent to one skilled in the art based on the present disclosure.

In certain preferred embodiments, a gaseous agent, for example, air or a perfluorocarbon gas, is combined with a liquid perfluorocarbon, such as perfluorohexane, perfluoroheptane, perfluorooctylbromide (PFOB), perfluorodecalin, perfluorododecalin, perfluorooctyliodide, perfluorotripropylamine and perfluorotributylamine.

A preferred composition for use in the intracellular delivery of a bioactive agent, for example, genetic material, comprises a bioactive agent, a perfluorocarbon gas and a gaseous precursor which has a boiling point of greater than about 37° C., such as perfluoropentane. As discussed in detail below, energy, for example, heat or ultrasound, is preferably applied to the patient after the administration of the composition and to assist in the intracellular delivery of the bioactive agent.

The gaseous substances and/or gaseous precursors are preferably incorporated in the cationic lipid compositions of the present invention irrespective of the physical nature of the composition. Thus, it is contemplated that the gaseous substances and/or precursors thereto are incorporated in compositions which are suspensions/emulsions or vesicular compositions, including micelles and liposomes. Incorporation of the gaseous substances and/or precursors thereto in the cationic lipid compositions may be achieved by using any of a number of methods. For example, the formation of gas-filled vesicles can be achieved by shaking or otherwise agitating an aqueous mixture which comprises a gas or gas precursor and the cationic lipids of the present invention.

This promotes the formation of stabilized vesicles within which the gas or gas precursor is encapsulated. Gas or gaseous precursor cationic lipid compositions may be prepared in other manners similar to those discussed in connection with the incorporation of bioactive agents in vesicular compositions as earlier discussed.

The gaseous substances and/or precursors thereto may also be incorporated in the cationic lipid compositions using any conventional and well-known techniques. For example, a gas may be bubbled directly into an aqueous mixture of the present cationic lipid compounds, optionally in the presence of a bioactive agent. Alternatively, a gas instillation method can be used as disclosed, for example, in U.S. Pat. Nos. 5,352,435 and 5,228,446, the disclosures of each of which are hereby incorporated herein by reference in their entireties. Suitable methods for incorporating the gas or gas precursor in cationic lipid compositions are disclosed also in U.S. Pat. No. 4,865,836, the disclosure of which is hereby incorporated herein by reference. Other methods would be apparent to one skilled in the art based on the present disclosure.

In preferred embodiments, the gaseous substances and/or gaseous precursor materials are incorporated in vesicular compositions, with micelles and liposomes being preferred. Liposomes are particularly preferred because of their high stability and biocompatability. As discussed in detail below, vesicles in which a gas or gas precursor or both are encapsulated are advantageous in that they can be more easily monitored in vivo, for example, by monitoring techniques which involve ultrasound. Thus, the circulation and delivery of the vesicles to the targeted tissue and/or cells can be observed via a non-invasive procedure. Gas precursor- or gas-filled vesicles are preferred also because the application of high energy ultrasound, radio frequency, optical energy, for example, laser light, and/or heat, to produce areas of hyperthermia, can be used to rupture in vivo the vesicles and thereby promote release of the entrapped gas (or precursor thereto) and bioactive agent. Thus, vesicular compositions permit the controlled release of a bioactive agent in vivo.

In addition to being entrapped within the vesicle, it is contemplated that the bioactive agent may be located also, or instead of, outside of the vesicles or in the lipid membranes. Thus, in certain embodiments, the bioactive agent may be coated on the surface of the liposomes or micelles and/or in the lipid membranes, in addition to, or instead of, being entrapped within the vesicles.

The bioactive agent which is incorporated in the present cationic lipid compositions is preferably a substance which is capable of exerting a therapeutic biological effect in vitro and/or in vivo. Particularly suitable bioactive agents for use in the methods and compositions of the present invention is genetic material. Examples of genetic materials include, for example, genes carried on expression vectors, such as plasmids, phagemids, cosmids, yeast artificial chromosomes (YACs) and defective- or "helper" viruses; anti-sense and sense oligonucleotides; phosphorothioate oligodeoxynucleotides; antigene nucleic acids; and single and double stranded RNA and DNA, including DNA which encodes at least a portion of a gene, for example, DNA which encodes for human leukocyte antigen (HLA), dystrophin, cystic fibrosis transmembrane receptor (CFTR), interleukin-2 (IL-2), tumor necrosis factor (TNF) and granulocyte-macrophage colony stimulating factor (GMCSF). The DNA can also encode certain proteins which may be used in the treatment of various types of pathologies or conditions, including those which are associated with the loss or deterioration of immune competence. Such pathologies or conditions involving immune competence include, for example, acquired immune deficiency syndrome (AIDS), cancer, chronic viral infections, and autoimmune disease.

Specifically, DNA may be selected which expresses adenosine deaminase (ADA) for the treatment of ADA deficiency; growth hormone for the treatment of growth deficiency or to aid in the healing of tissues; insulin for the treatment of diabetes; luteinizing hormone releasing hormone (LHRH) antagonist as a birth control agent; LHRH for the treatment of prostate or breast cancer; tumor necrosis factor and/or interleukin-2 for the treatment of advanced cancers; high-density lipoprotein (HDL) receptor for the treatment of liver disease; thymidine kinase for the treatment of ovarian cancer, brain tumors, or human immunodeficiency virus (HIV) infection; HLA-B7 for the treatment of malignant melanoma; IL-2 for the treatment of neuroblastoma, malignant melanoma or kidney cancer; interleukin-4 (IL-4) for the treatment of cancer; HIV env for the treatment of HIV infection; antisense ras/p53 for the treatment of lung cancer; and Factor VIII for the treatment of Hemophilia B. Such therapies are described, for example, in *Science*, Vol. 258, pp. 744–746 (1992), the disclosure of which is incorporated herein by reference in its entirety.

As noted above, the present invention provides cationic lipid formulations which comprise cationic lipid compositions in combination with one or more bioactive agents. The cationic lipid compositions may comprise cationic suspensions/emulsions and/or cationic vesicular compositions, including cationic liposome compositions and/or cationic micelle compositions. In addition, the cationic lipid compositions can comprise one or more cationic lipid compounds optionally in combination with a stabilizing material, such as an amphipathic compound, and a gas or precursor thereto. These cationic lipid formulations may be prepared according to any of a variety of techniques. For example, the cationic lipid formulations may be prepared from a mixture of cationic lipid compounds, bioactive agent and gas or gaseous precursor. In the case of vesicular compositions, it is contemplated that the bioactive agent is entrapped within the vesicle of the liposome or micelles. In certain cases, the bioactive agent can be incorporated also into the membrane walls of the vesicle. In the case of a suspension/emulsion, it is contemplated that the bioactive agent is generally dispersed homogeneously throughout the suspension/emulsion. Alternatively, the cationic lipid compositions may be preformed from cationic lipid compounds and gas or gaseous precursor. In the latter case, the bioactive agent is then added to the lipid composition prior to use. For example, an aqueous mixture of liposomes and gas may be prepared to which the bioactive agent is added and which is agitated to provide the cationic liposome formulation. The cationic liposome formulation is readily isolated also in that the gas- and/or bioactive agent-filled liposome vesicle generally float to the top of the aqueous solution. Excess bioactive agent can be recovered from the remaining aqueous solution.

The formulations of the present invention can be used in either in vitro or in vivo applications. In the case of in vitro applications, including cell culture applications, the cationic lipid formulations can be added to the cells in cultures and then incubated. If desired, where liposomes are employed, energy, such as sonic energy, may be applied to the culture media to burst the liposomes and release any therapeutic agents.

With respect to in vivo applications, the formulations of the present invention can be administered to a patient in a variety of forms adapted to the chosen route of administration, namely, parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration.

It is contemplated that the present cationic lipid formulations can be administered also by coating a medical device, for example, a catheter, such as an angioplasty balloon catheter, with a cationic lipid formulation. Coating may be achieved, for example, by dipping the medical device into a cationic lipid formulation or a mixture of a cationic lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a cationic lipid formulation may be specifically bound to the surface of the device. Such binding techniques are described, for example, in K. Ishihara et al., *Journal of Biomedical Materials Research*, Vol. 27, pp. 1309–1314 (1993), the disclosures of which are incorporated herein by reference in their entirety.

The useful dosage to be administered and the particular mode of administration will vary depending upon such factors as the age, weight and the particular animal and region thereof to be treated, the particular bioactive agent and cationic lipid compound used, the therapeutic or diagnostic use contemplated, and the form of the formulation, for example, suspension, emulsion, micelle or liposome, as will be readily apparent to those skilled in the art. Typically, dosage is administered at lower levels and increased until the desirable therapeutic effect is achieved. The amount of cationic lipid compound that is administered can vary and generally depends upon the amount of bioactive agent being administered. For example, the weight ratio of cationic lipid compound to bioactive agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular bioactive agent, and about 1 mg to about 100 mg of the cationic lipid compositions, each per kilogram of patient body weight, is administered, although higher and lower amounts can be used.

After vesicular lipid formulations which comprise a gas or gaseous precursor and bioactive agent have been administered to a patient, energy, preferably in the form of ultrasonic energy, can be applied to the target tissue to identify the location of the vesicles containing gas or gaseous precursor and bioactive agent. The applied energy may also be employed to effect release of the bioactive agent and facilitates cellular uptake of the bioactive agent. As one skilled in the art would recognize, this method of mediating cellular transfection with ultrasonic energy is preferably effected with tissues whose acoustic window permits the transmission of ultrasonic energy. This is the case for most tissues in the body, including muscle and organ tissues, such as the heart and liver, as well as most other vital structures. With respect to brain tissue, it may be necessary to create a "surgical window" by removing part of the skull, inasmuch as ultrasonic energy generally does not transmit through bone. Intravascular and/or endoluminal ultrasound transducers may be used to apply the ultrasound energy to selected tissues and/or sites in the body, for example, the aorta and the esophagus.

Cationic lipid formulations can be formulated to be sufficiently stable in the vasculature such that they circulate throughout the body and provide blood pool equilibration. As one skilled in the art would recognize, the lipid formulations, including those which comprise suspensions/emulsions and vesicles, such as liposomes and micelles, may be coated with certain materials to minimize uptake by the reticuloendothelial system. Suitable coatings include, for example, gangliosides and glycolipids which bind saccharide moieties, such as glucuronate, galacturonate, guluronate, poly(ethylene glycol), poly(propylene glycol), polyvinylpyrrolidone, poly(vinyl alcohol), dextran, starch, phosphorylated and sulfonated mono-, di-, tri-, oligo- and polysaccharides and albumin. Provided that the circulation half-life of the cationic lipid formulations is of a sufficient period of time, they will generally pass through the target tissue while passing through the body. In the case of lipid formulations which comprise gas or gaseous precursors, energy, for example, sonic energy, may be focused on the tissue to be treated, for example, diseased tissue. The bioactive agent will then be released locally in the target tissue. The inventors have found also that antibodies, carbohydrates, peptides, glycopeptides, glycolipids and lectins also assist in the targeting of tissue with the lipid formulations and the bioactive agents. Accordingly, these materials may be incorporated into the lipid formulations also.

Ultrasound can be used for both diagnostic and therapeutic purposes. In general, the levels of energy from diagnostic ultrasound are insufficient to cause rupture of vesicular species and to facilitate release and cellular uptake of the bioactive agents. Moreover, diagnostic ultrasound involves the application of one or more pulses of sound. Pauses between pulses permits the reflected sonic signals to be received and analyzed. The limited number of pulses used in diagnostic ultrasound limits the effective energy which is delivered to the tissue that is being studied.

On the other hand, higher energy ultrasound, for example, ultrasound which is generated by therapeutic ultrasound equipment, is generally capable of causing rupture of the vesicular species. In general, therapeutic ultrasound machines use from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicular species, continuous wave ultrasound is preferred, although the sound energy may be pulsed also. If pulsed sound energy is used, the sound will generally be pulsed in echo train lengths of about 8 to about 20 or more pulses at a time. Preferably, the echo train lengths are about 20 pulses at a time. In addition, the frequency of the sound used may vary from about 0.25 to about 100 megahertz (MHz). In general, frequency for therapeutic ultrasound ranges between about 0.75 and about 3 MHz are preferred with about 1 and about 2 MHz being more preferred. In addition, energy levels may vary from about 0.05 Watt (W) to about 5.0 W, with energy levels of about 0.1 to about 0.5 W being preferred. For very small vesicular species, for example, species in which the vesicles have a diameter of less than about 0.5 micron, higher frequencies of sound are generally preferred. This is because smaller vesicular species are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, for deep structures it is generally necessary to focus the ultrasonic energy so that it is preferentially directed within a focal zone. Alternatively, the ultrasonic energy may be applied via interstitial probes, intravascular ultrasound catheters or endoluminal catheters. Such probes or catheters may be used, for example, in the esophagus for the diagnosis and/or treatment of esophageal carcinoma.

The present invention is further described in the following examples. In these examples, examples 1 to 9 are actual examples. Examples 10 to 12 are prophetic examples. These examples are for illustrative purposes only, and are not to be construed as limiting the appended claims.

Various of the starting materials used in the following examples are commercially available. N,N-dimethylethylenediamine and iodomethane were purchased from Aldrich Chemical Co. (Milwaukee, Wis.).

EXAMPLE 1

Synthesis of N,N'-Bis (dodecylaminocarbonylmethylene)-N,N-'-bis (β-N,N, N-trimethylammoniumethylaminocarbonylmethylene)-N,N'-dimethylethylenediamine tetraiodide (EDTA-LA-TMA tetraiodide)

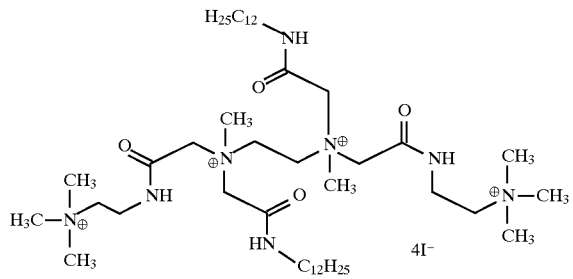

Synthetic Route (i) Synthesis of N,N'-Bis (dodecylaminocarbonylmethylene)-ethylenediamine-N,N'-diacetic acid (EDTA-LA)

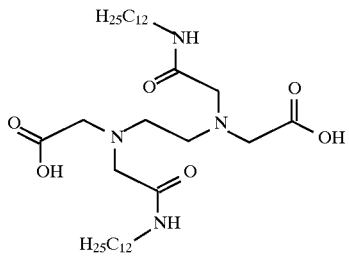

Dodecylamine (3.71 g, 0.02 mole) in dry methanol (60 mL) was added to a suspension of ethylenediaminetetraacetic acid dianhydride (2.56 g, 0.01 mole) in dry methanol (30 mL). The mixture was stirred at 50° C. for 6 hours. The resulting white solid precipitate was isolated by filtration and dried under vacuum at room temperature to yield 3.43 g (64%) of the title compound. m.p. 156°–158° C.

IR: 3320 cm$^{-1}$ for OH; 1670 cm$^{-1}$ for —C(=O)—.

(ii) Synthesis of N,N'-Bis (dodecylaminocarbonylmethylene)-N,N'-bis(β-N,N-dimethylaminoethylaminocarbonylmethylene) ethylenediamine (EDTA-LA-DMA)

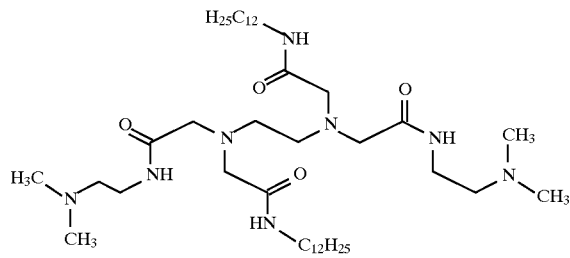

EDTA-LA (3.14 g, 0.005 mole) from step (i), N,N-dimethylethylenediamine (0.88 g, 0.01 mole) and CHCl$_3$ (100 mL) were combined. After dissolution of the solid materials, the solution was cooled to 50° C. and a solution of 1,3-dicyclohexylcarbodiimide (DCC) (2.227 g, 0.011 mole) in CHCl$_3$ (20 mL) was added dropwise. A precipitate was observed. The reaction mixture was stirred at room temperature for about 24 hours. The reaction mixture was filtered and the filtrate was washed with 0.5N acetic acid (100 mL) to decompose any excess DCC. A white milky solution was formed which separated into two layers. The bottom organic layer was dried (Na$_2$SO$_4$) and concentrated in vacuo to yield 3.81 g of the title compound as a soft solid.

IR: 3280 cm-1; 2900 cm$^{-1}$; 1640 cm$^{-1}$; 1530 cm$^{-1}$.

(iii) Synthesis of EDTA-LA-TMA Tetraiodide

A solution of EDTA-LA-DMA (3.66 g, 4.77 mmole) from step (ii), iodomethane (3.41 g, 24 mmole) and ethanol (30 mL) was refluxed for 2 hours. The ethanolic solution was concentrated in vacuo and the resulting residue was lyophilized overnight. 3.98 g of EDTA-LA-TMA tetraiodide, a compound within the scope of the invention, was obtained as a yellow solid.

IR: 3260 cm$^{-1}$; 1650 cm$^{-1}$.

EXAMPLE 2

Synthesis of N,N"-Bis (hexadecylaminocarbonylmethylene)-N,N'N"-tris(β-N,N, N-trimethylammoniumethylaminocarbonylmethylene)-N,N',N"-trimethyldiethylenetriamine hexaiodide (DTPA-HA-TME Hexaiodide)

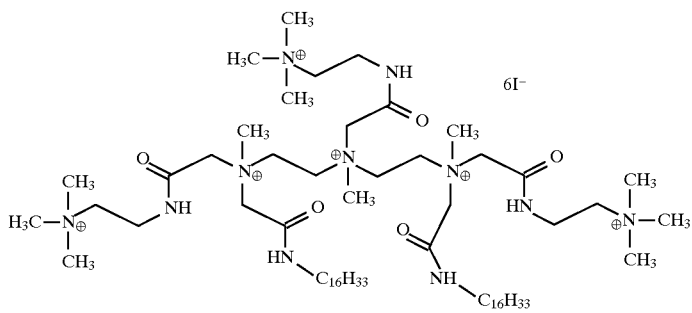

Synthetic Route

(i) Synthesis of N,N"-Bis (hexadecylaminocarbonylmethylene)-diethylenetriamine-N,N',N"-triacetic acid (DTPA-HA)

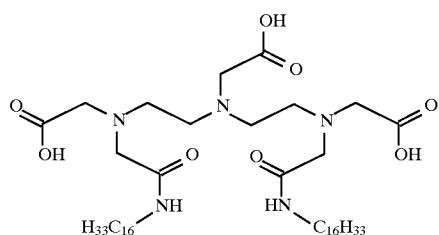

Hexadecylamine (4.82 g, 0.02 mole) in dry methanol (60 mL) was added to a suspension of diethylenetriamine pentaacetic acid dianhydride (3.57 g, 0.01 mole) in dry methanol (30 mL). The resulting mixture was stirred at 50° C. for 6 hours. The reaction mixture was cooled and the resulting white solid precipitate was collected by filtration. The white solid was dried under vacuum to yield 5.9 g of the title compound.

(ii) Synthesis of N,N"-Bis (hexadecylaminocarbonylmethylene)-N,N',N"-tris(β-N,N-dimethylaminoethylaminocarbonylmethylene) diethylenetriamine (DTPA-HA-DMA)

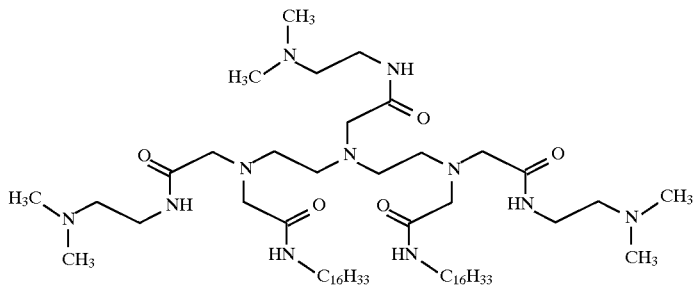

A solution of DTPA-HA (4.2 g, 0.005 mole) from step (i), N,N-dimethylethylenediamine (0.88 g, 0.01 mole) and CHCl₃ (100 mL) was cooled to 0°–5° C. To this solution was added dropwise a solution of DCC (2.23 g, 0.011 mole) in CHCl₃ (20 mL). The reaction mixture was stirred for 24 hours at room temperature. The resulting precipitate was removed by filtration and was washed with 0.5% acetic acid (100 mL). A white, milky solution was obtained which was filtered again, dried (Na₂SO₄), and concentrated in vacuo. The title compound was obtained as a soft solid (3.5 g).

(iii) Synthesis of DTPA-HA-TMA Hexaiodide

A solution of DTPA-HA-DMA (4.7 g, 4.8 mmole) from step (ii), iodomethane (3.41 g) and methanol (50 mL) was refluxed for 2 hours. The methanolic solution was concentrated in vacuo and the resulting residue was lyophilized overnight. 6 g of DTPA-HA-TME hexaiodide, a compound within the scope of the invention, was obtained as a yellow solid.

EXAMPLE 3

Synthesis of N,N'-Bis (dodecylaminocarbonylmethylene)-N,N'-bis(β-N,N,N-trimethylammoniumethylaminocarbonylmethylene)-N, N'-dimethyl cyclohexylene-1,4-diamine tetraiodide (CDTA-LA-TMA Tetraiodide)

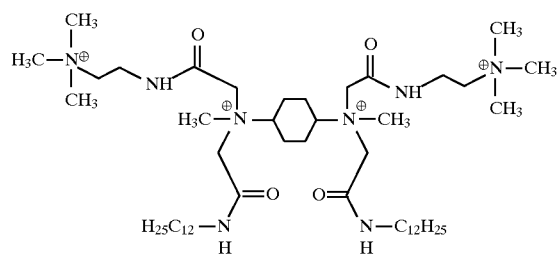

Synthetic Route (i) Synthesis of N,N'-Bis (dodecylaminocarbonylmethylene)-cyclohexylene-1,4-diamine-N,N'-diacetic acid (CDTA-LA)

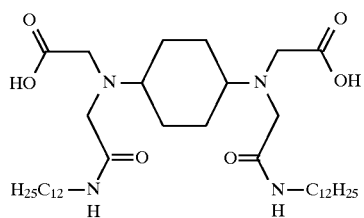

A solution of dodecylamine (3.71 g, 0.02 mole) in dry methanol (60 ml) was added to a suspension of cyclohexane-1,4-diamine-N,N,N',N'-tetraacetic acid dianhydride (3.1 g, 0.01 mole) in dry methanol (30 mL). The resulting mixture was stirred at 50° C. for 6 hours. Filtration yielded the title compound (4.8 g) as a white solid.

(ii) Synthesis of N,N'-Bis (dodecylaminocarbonylmethylene)-N,N'-bis(β-N,N-dimethylaminoethylaminocarbonyl methylene) cyclohexylene-1,4-diamine (CDTA-LA-DMA)

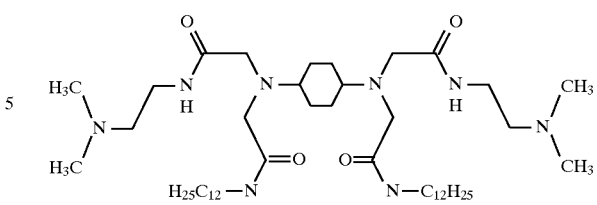

A solution of CDTA-LA (3.4 g, 0.005 mole) from step (i), N,N-dimethylethylenediamine (0.88 g, 0.01 mole) and CHCl$_3$ (100 mL) was cooled to 0°–5° C. To this solution was added dropwise a solution of DCC (2.23 g, 0.011 mole) in CHCl$_3$ (20 mL). The reaction mixture was stirred for 24 hours at room temperature and filtered. The filtrate was washed with 0.5% acetic acid (100 mL) to decompose any excess DCC and was filtered again. The filtrate was dried (Na$_2$SO$_4$) and concentrated in vacuo to yield the title compound (4.2 g) as a soft solid.

(iii) Synthesis of CDTA-LA-TMA Tetraiodide

A solution of CDTA-LA-DMA (3 g) from step (ii), iodomethane (3.5 g) and methanol (30 mL) was refluxed for 2 hours. The methanolic mixture was concentrated in vacuo and the resulting residue was lyophilized overnight. 3.1 g of CDTA-LA-TMA tetraiodide, a compound within the scope of the invention, was obtained as a solid.

EXAMPLE 4

Synthesis of 1,1,7,7-tetra(β-N,N,N,N-tetramethylammoniumethylaminocarbonylmethylene)-4-hexadecylaminocarbonylmethylene-N,N',N''-trimethyl-1,4,7-triazaheptane heptaiodide (DTPA-MHA-TTMA Heptaiodide)

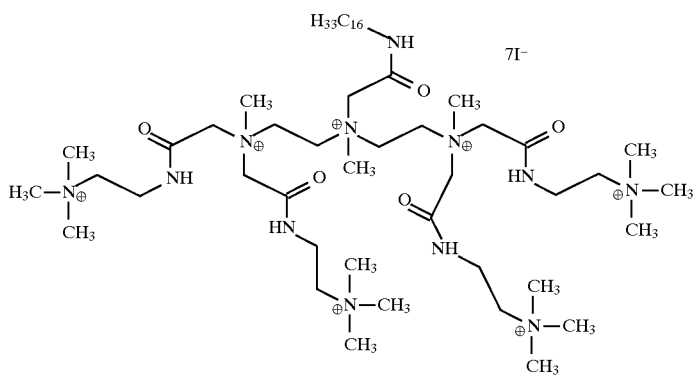

Synthetic Route (i) Synthesis of 4-hexadecylaminocarbonylmethylene-1,4,7-triazaheptane-1,1,7,7-tetraacetic acid (DTPA-MHA)

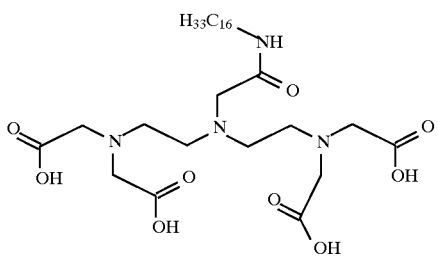

A solution of diethylenetriaminepentaacetic acid (3.93 g, 0.01 mole), hexadecylamine (2.4 g, 0.01 mole) and CHCl₃ (200 mL) was cooled to 0°–50° C. To this solution was added dropwise a solution of DCC (2.23 g, 0.011 mole) in CHCl₃ (15 mL). The reaction mixture was stirred for 24 hours at room temperature and filtered. The filtrate was washed with 0.5% acetic acid (100 mL) and filtered again. The filtrate was dried (Na₂SO₄) and concentrated in vacuo. Recrystallization of the resulting residue from water yielded the title compound as a white solid (3.7 g).

(ii) Synthesis of 1,1,7,7-tetra(β-N,N-dimethylaminoethylaminocarbonylmethylene)-4-hexadecylaminocarbonylmethylene)-1,4,7-triazaheptane (DTPA-MHA-TDMA)

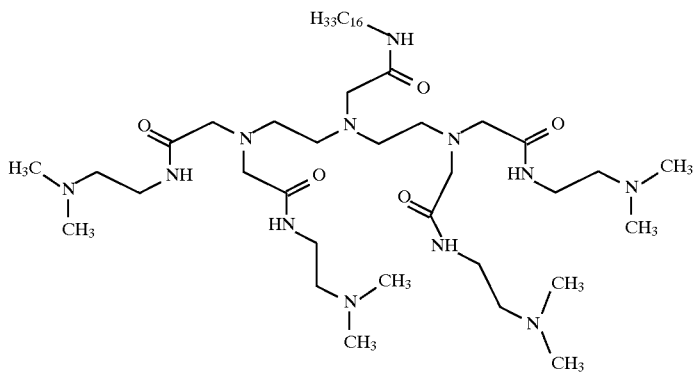

A solution of DTPA-MHA (3 g) from step (i), N,N-dimethylethylenediamine (1.76 g) and CHCl₃ (200 mL) was cooled to 0°–5° C. To this solution was added dropwise a solution of DCC (4.5 g, 0.02 mole) in CHCl₃ (20 mL). The reaction mixture was stirred overnight at room temperature. The resulting precipitate was collected by filtration and the filtrate was washed with 0.5% acetic acid (100 mL) and filtered again. The filtrate was dried (Na₂SO₄) and concentrated in vacuo. The resulting residue was purified on a silica gel column. The title compound was obtained as a soft solid (2.8 g).

(iii) Synthesis of DTPA-MHA-TTMA Heptaiodide

A solution of DTPA-MHA-TDMA (2.24 g), iodomethane (3.5 g, 0.03 mole) and methanol (30 mL) was refluxed for 2 hours. The methanolic solution was concentrated in vacuo and the resulting residue was lyophilized overnight to yield 2.4 g of DTPA-MHA-TTMA heptaiodide, a compound within the scope of the present invention.

EXAMPLE 5

Using procedures similar to those in Examples 1 to 4, the following compounds within the scope of the invention were prepared.

EXAMPLE 5A

N,N'-Bis(dodecyloxycarbonylmethylene)-N,N'-bis(β-N,N, N-trimethylammoniumethylaminocarbonylmethylene) ethylenediamine diiodide

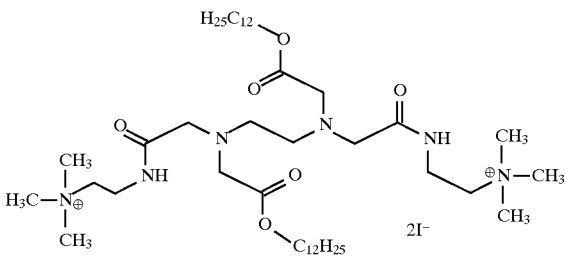

EXAMPLE 5B

N,N",N"-Tetra(β-N,N,N-trimethylammoniumethylaminocarbonylmethylene)-N'-(1,2-dioleoylglycero-3-phosphoethanolaminocarbonylmethylene) diethylenetriamine tetraiodide

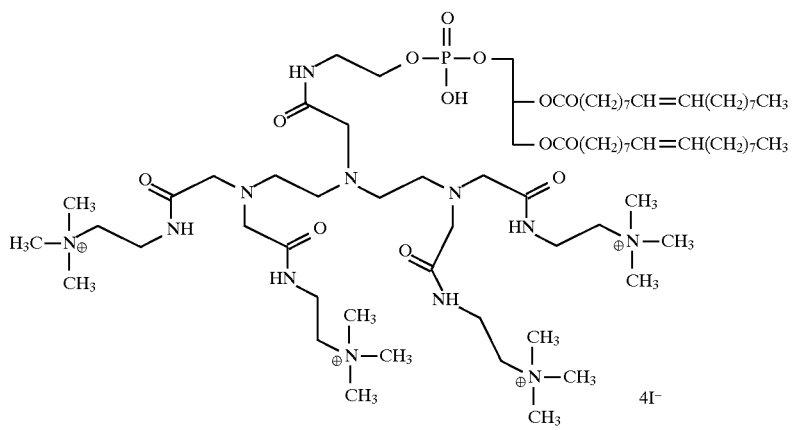

EXAMPLE 5C

N,N'-Bis(hexadecylaminocarbonylmethylene-N,N'-bis(trimethylammoniumethylaminocarbonyl methylene)ethylenediamine diiodide

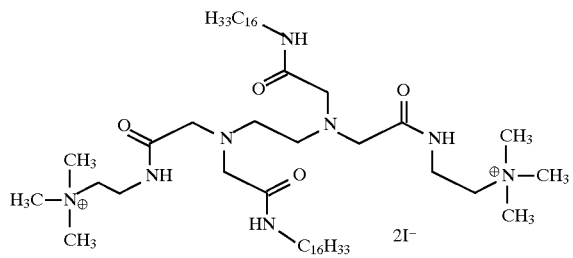

EXAMPLE 5D

N,N'-bis(hexadecyloxycarbonylmethylene)-N-(β-N, N, N-trimethylammoniumethylaminocarbonylmethylene)-N-methyl-N'-(carboxymethylene)ethylenediamine diiodide

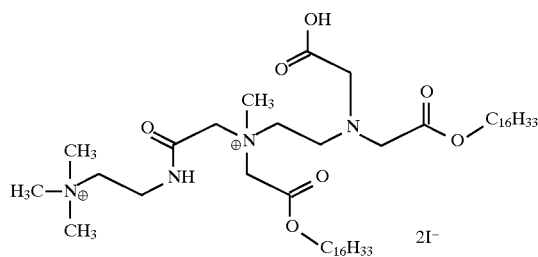

EXAMPLE 5E

N,N'-bis(hexadecylaminocarbonylmethylene)-N,N'-bis(β-N,N,N-trimethylammoniumethylaminocarbonyl methylene)-N,N'-dimethylethylenediamine tetraiodide

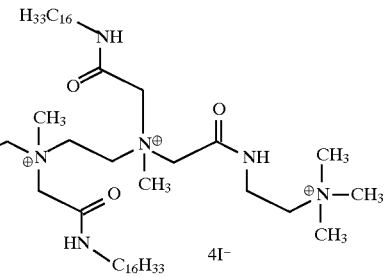

Formulations of this invention are subjected to various biological tests, the results of which correlate to useful therapeutic activity. These tests are useful in determining the ability of the present formulations to deliver intracellularly bioactive agents, including genetic material. These tests are useful also in determining the ability of the present formulations to treat genetic diseases, including diseases which involve a pathology or condition which is associated with loss or deterioration of immune competence.

EXAMPLE 6

The following examples are directed to the intracellular delivery of genetic material with cationic lipid compounds of the present invention and compounds disclosed in the prior art. The genetic material involved in these transfection studies is DNA that codes for Chloramphenicol Acetyl Transferase ("CAT"). The amount of expressed CAT (nanograms per mL (ng/mL)) was assayed using the Boehringer Mannheim CAT ELISAT™ kit, the results of which are tabulated in FIGS. 1 and 2.

LIPOFECTAMINE™ and LIPOFECTIN® were purchased from Gibco BRL, a division of Life Technologies, Inc. (Gaithersburg, Md.). LIPOFECTAMINE™ is a 3:1 liposome formulation of N-[2-({2,5-bis(3-aminopropyl)amino]-1-oxypentyl}amino)ethyl-N,N-dimethyl-2,3-bis(9-octadecenyloxy)-1-propanaminium trifluoroacetate and dioleoylphosphatidylethanolamine ("DOPE"). LIPOFECTIN® is a liposome formulation of N-[1-(2,3-dioleoyloxy)propyl]-N,N,N-trimethylammonium chloride ("DOTMA") and DOPE. (See *Proc. Natl. Acad. Sci. USA*, Vol. 84, p. 7413 (1987).) TRANSFECTAM™ was purchased from Promega Corp (Madison, Wis.). TRANSFECTAM™ is a cationic lipopolyamine compound which comprises a spermine headgroup. (See *Proc. Natl. Acad. Sci.*, Vol. 86, p. 6982 (1989); *J. Neurochem.*, Vol. 54, p. 1812 (1990); and *DNA and Cell Biology*, Vol. 12, p. 553 (1993).) "DOTAP" refers to 1,2-dioleoyl-3-propyl-N,N,N-trimethylammonium halide.

EXAMPLE 6A

This example describes the biological testing of the compounds prepared in Examples 5C and 5D, Lipofectin, Lipofectamine and DOTAP and Transfectam in the absence of serum.

HeLa cells (American Type Culture Collection, Rockville, Md.) were cultured in EMEM media (Mediatech, Washington, D.C.). The cells were grown in 6-well plates (Becton Dickinson, Lincoln Park, N.J.) and at a density of $4\times10^5$ cells/well until they were 60–80% confluent in a VWR model 2500 $CO_2$ incubator (VWR, Philadelphia, Pa.). DNA (1.7 µg) was diluted to 50 µL in HEPES buffered saline (HBS) (HEPES 20 mM, 150 mM NaCl, pH 7.4) for each well to be infected. 10 µL solutions of the cationic lipid compounds prepared in Examples 5C and 5D, Lipofectin, Lipofectamine, DOTAP and Transfectam were each diluted to 50 µL in HBS. The DNA and lipid solutions were mixed by inverting and incubated at room temperature for 15 minutes. After incubating, each of the mixtures of DNA and cationic lipid (100 µL) was added to 1.9 mL of media without serum and mixed by inverting. The media was removed from the 6-well plates and replaced with the media containing lipid and DNA. The cells were then incubated in a $CO_2$ atmosphere at 37° C. for 5–6 hours. After incubating, the lipid/DNA media was removed and replaced with complete media. The cells were then incubated for 48–72 hours and the level of expressed protein was assayed. The results of the assay were measured using an SLT Labinstruments SPECTRA Shell plate reader (SLT, Salzburg, Austria) which was linked to a Centris 650 computer (Apple Computer, Inc., Cupertino, Calif.) and controlled using DeltaSoft II version 4.13s (Biometallics, Inc., Princeton, N.J.). The results of the assay are depicted in FIG. 1 which show increased expression of CAT when the cationic lipid compounds of the present invention are used to transfect cells, relative to compounds of the prior art. Accordingly, the experiments performed in this example demonstrate that the cationic lipid compounds of the present invention provide useful and improved transfection of cells with bioactive agents as compared to compounds of the prior art.

EXAMPLE 6B

This example describes the biological testing of the compound prepared in Example 5D, Lipofectin and Lipofectamine in the presence of serum.

HeLa cells were cultured in 4 mL of culture media as described above, except that the media was supplemented with enriched calf serum (Gibco BRL Life Technologies, Gaithersburg, Md.) and Penicillin/Streptomycin (Boehringer Mannheim Biochemicals (BMB), Indianapolis, Ind.). The cells were grown in 6-well plates (Becton Dickinson, Lincoln Park, N.J.) and at a density of $4\times10^5$ cells/well until they were 60–80% confluent in a VWR model 2500 $CO_2$ incubator (VWR, Philadelphia, Pa.). DNA (3.3 µg) was diluted to 100 µL in HEPES buffered saline (HBS) (HEPES 20 mM, 150 mM NaCl, pH 7.4) for each well to be infected.

20 µL solutions were prepared of (1) the cationic lipid compound of Example 5D in combination with varying amounts of DOPE; (2) Lipofectin; and (3) Lipofectamine. These were diluted to 100 µL in HBS for each well. The compound of Example 5D and DOPE were combined in weight ratios of 5:1, 6:1, 7:1, 9:1, 11:1 and 14:1. The DNA and lipid solutions were mixed by inverting and incubated at room temperature for 15 minutes. After incubating, the mixtures of DNA and cationic lipid (200 µL) were added to each well (except for a HeLa (CELLS) standard to which no DNA with cationic lipid was added) and the mixtures were agitated by pipetting several times upwards and downwards. The cells were then incubated in a $CO_2$ atmosphere at 37° C. for 48–72 hours. After incubating, the protein level was assayed as described above.

The results of the assay are depicted in FIG. 2 which show increased expression of CAT when the cationic lipid compounds of the present invention are used to transfect cells, relative to compounds of the prior art. Particularly desirable transfection is observed in compositions which comprise a 6:1 ratio of the compound of Example 5D to DOPE. The experiments performed in this example demonstrate that the cationic lipid compounds of the present invention provide improved transfection of cells with bioactive agents as compared to compounds of the prior art.

EXAMPLE 7

In vivo experiments in rats were performed which demonstrate the high effectiveness of the present cationic lipid compounds to deliver intracellularly genetic material. The experiments demonstrate also the effectiveness of using ultrasound energy for targeting specific tissue in vivo with vesicular compositions containing genetic material.

Plasmid pSV β-gal (Promega, Madison, Wis.) which contains the β-galactosidase gene was combined with the cationic lipid compound prepared in Example 5D by mixing. The resulting mixture was injected into each of three Sprague Dawley rats (rats (A), (B) and (C)) via the tail vein. Rat (A) was not subjected to ultrasound. Ultrasonic energy was applied to the inside of the hind leg during injection for each of rats (B) and (C). After 48 hours, the rats were euthanized and the tissues were removed. The tissues were fixed for 72 hours in 2% formalin, sliced thin and placed in an X-gal solution. After 16 hours at 37° C., the tissues were inspected. The tissue from rat (A) exhibited a blue color which is indicative of general transfection. The tissue from rats (B) and (C) exhibited blue color only at the site where ultrasound energy was applied. This indicates that localization of gene expression can be achieved with the compounds and methods of the present invention.

EXAMPLE 8

A cationic lipid composition according to the present invention was prepared from six parts of the compound prepared in Example 5D and 1 part dipalmitoylphosphatidylethanolamine (DPPE) labeled with rhodamine (Avanti Polarlipids, Alabaster, Ala.). The cationic lipid composition was dissolved in ethanol and a Mansfield angioplasty catheter tip (Boston Scientific Corp., Watertown, Mass.) was dipped into the ethanolic formulation, removed and allowed to dry. This procedure was repeated three times. The coated catheter tips were then placed onto a Nikon light microscope equipped with a filter for rhodamine fluorescence. A control catheter, which was not coated with the cationic lipid composition, was also placed onto the light microscope. Fluorescence of the coated catheter tips was observed, whereas the control catheter tips did not fluoresce. This confirmed the presence of a coating of the lipid composition on each of the coated catheters. The coated catheter tips were then dipped into normal saline, water and human serum for varying periods of time and viewed under the light microscope. Fluorescence of the catheter tips was observed again. This demonstrated that the coating of the rhodamine-labeled lipid composition adhered to the surface of the catheters. Accordingly, lipid compositions of the present invention can be delivered to specific locations within the body by coating the compositions onto catheters which are then administered to a patient, as appropriate.

EXAMPLE 9

A cationic lipid formulation according to the present invention was prepared from DNA (5 μg) fluorescently labelled with fluorescein-12 DUTP (deoxyuracil triphosphate, commercially available from Boehringer Mannheim Biochemicals (BMB), Indianapolis, Ind.) using PCR, six parts of the compound prepared in Example 5D and 1 part DPPE. Catheters were subsequently dipped into ethanolic solutions of the cationic lipid formulation as described (for the compositions) in Example 8. A control catheter was not coated with the subject cationic lipid formulation. Fluorescence was induced and observed for the coated catheters as described in Example 8. No fluorescence was observed with the control catheter. This demonstrated that the cationic lipid formulations of the present invention adhere to the surface of catheters. Accordingly, lipid formulations of the present invention can be delivered to specific locations within the body by coating the formulations onto catheters which are then administered to a patient, as appropriate.

EXAMPLE 10

A cationic lipid formulation according to the present invention will be prepared from 6 parts of the compound of Example 5D, 1 part DPPE (dipalmitoyl-phosphatidylethanolamine) and 10 μg of plasmid DNA containing the gene for endothelial cell growth factor and a Respiratory Syncytial Virus RSV) growth factor. The formulation will be lyophilized, and 1 to 10 μg of the lyophilized formulation will be coated on a balloon of an angioplasty catheter. Coating will be accomplished by simply dipping the balloon into the formulation. The angioplasty catheter will be introduced into the left anterior descending coronary artery of a patient to cross the region of a hemodynamically significant stenosis. The catheter will be inflated to 6 atmospheres of pressure with the coated balloon. The stenosis will be alleviated and the lyophilized coating on the balloon will be deposited on the arterial wall. Transfection of endothelial cells results in localized production of endothelial cell growth factor. Healing of the arterial wall will be improved and fibroblast proliferation will be reduced, resulting also in lessened restenosis.

EXAMPLE 11

The procedure described in Example 10 will be repeated except that the surface of the catheter balloon will be modified to improve the binding of the lyophilized cationic lipid formulation according to the procedure described in K. Ishihara et al., *Journal of Biomedical Materials Research*, Vol. 27, pp. 1309–1314 (1993).

EXAMPLE 12

The procedure described in Example 10 will be repeated except that a vascular stent comprising, for example, DACRON™ (a polyester synthetic fiber) and/or wire mesh, is substituted for the angioplasty catheter. Improved endothelialization is obtained along the surface of the stent.

We claim:

1. A cationic lipid compound of the formula:

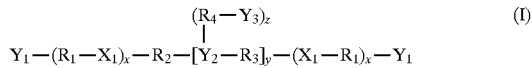

wherein:

each of x, y and z is independently an integer from 0 to about 100;

each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—;

each $X_2$ is independently O or S;

each $Y_1$ is independently a phosphate residue, N($R_6$)$_a$—, S($R_6$)$_a$—, P($R_6$)$_a$— or —$CO_2R_6$, wherein a is an integer from 1 to 3;

each $Y_2$ is independently —N($R_6$)$_b$—, —S($R_6$)$_b$— or —P($R_6$)$_b$—, wherein b is an integer from 0 to 2;

each $Y_3$ is independently a phosphate residue, N($R_6$)$_a$—, S($R_6$)$_a$—, P($R_6$)$_a$— or —$CO_2R_6$, wherein a is an integer from 1 to 3;

each of $R_1$, $R_2$, $R_3$ and $R_4$ is independently alkylene of 2 to about 20 carbons;

each $R_5$ is independently hydrogen or alkyl of 1 to about 10 carbons; and each $R_6$ is independently —[$R_7$—$X_3$]$_c$—$R_8$ or —$R_9$—[$X_4$—$R_{10}$]$_d$—Q, wherein:

each of c and d is independently an integer from 0 to about 100;

each Q is independently a phosphate residue, —N($R_{11}$)$_q$, —S($R_{11}$)$_q$, —P($R_{11}$)$_q$ or —$CO_2R_{11}$, wherein q is an integer from 1 to 3;

each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—;

each $R_7$ is independently alkylene of 2 to about 20 carbons;

each $R_8$ is independently hydrogen or alkyl of 1 to about 60 carbons;

each of $R_9$ and $R_{10}$ is independently alkylene of 2 to about 20 carbons; and each $R_{11}$ is independently —[$R_7$—$X_3$]$_c$—$R_8$ or —$R_9$—[$X_4$—$R_{10}$]$_d$—W, wherein:

each W is independently a phosphate residue, —N($R_{12}$)$_w$, —S($R_{12}$)$_w$, —P($R_{12}$)$_w$ or —$CO_2R_{12}$, wherein w is an integer from 1 to 3; and $R_{12}$ is —[$R_7$—$X_3$]$_c$—$R_8$; with the proviso that the compound of formula (I) comprises at least two quaternary salts.

2. The compound according to claim 1 wherein said quaternary salt comprises a pharmaceutically-acceptable counter ion.

3. The compound according to claim 2 wherein said counter ion is selected from the group consisting of halide, $R_{13}SO_3^-$, $R_{13}CO_2^-$, phosphate, sulfite, nitrate, gluconate, guluronate, galacturonate, estolate and mesylate, wherein $R_{13}$ is hydrogen, alkyl of 1 to about 20 carbons or aryl of about 6 to about 10 carbons.

4. The compound according to claim 1 wherein said compound is in lyophilized form.

5. The compound according to claim 1 wherein:

each of c, d, x, y and z is independently an integer from 0 to about 50;

each Q is independently a phosphate residue, $-CO_2R_{11}$ or $-N(R_{11})_q$, wherein q is 2 or 3; and each W is independently a phosphate residue, $-CO_2R_{12}$ or $-N(R_{12})_w$, wherein w is 2 or 3.

6. The compound according to claim 5 wherein:

each of q and w is 3.

7. The compound according to claim 6 wherein:

each of c, d, x, y and z is independently an integer from 0 to about 20; and $X_2$ is O.

8. The compound according to claim 7 wherein:

each of c, d, x, y and z is independently an integer from 0 to about 10; and each of $X_1$, $X_3$ and $X_4$ is independently $-C(=O)-NR_5-$, $-NR_5-C(=O)-$, $-C(=O)-O-$ or $-O-C(=O)-$.

9. The compound according to claim 8 wherein:

each of c, d, x, y and z is an integer from 0 to about 5.

10. The compound according to claim 9 wherein:

each of $R_1$, $R_2$, $R_3$ and $R_4$ is independently straight chain alkylene of 2 to about 10 carbons or cycloalkylene of about 4 to about 10 carbons;

each $R_5$ is independently hydrogen or alkyl of 1 to about 4 carbons;

each $R_7$ is independently alkylene of 2 to about 10 carbons;

each $R_8$ is independently hydrogen or alkyl of 1 to about 40 carbons; and each of $R_9$ and $R_{10}$ is independently alkylene of 2 to about 10 carbons.

11. The compound according to claim 10 wherein:

each of $R_1$, $R_2$, $R_3$ and $R_4$ is independently straight chain alkylene of 2 to about 4 carbons or cycloalkylene of about 5 to about 7 carbons;

$R_5$ is hydrogen;

each $R_7$ is independently alkylene of 2 to about 4 carbons;

each $R_8$ is independently hydrogen or alkyl of 1 to about 20 carbons; and each of $R_9$ and $R_{10}$ is independently alkylene of 2 to about 4 carbons.

12. The compound according to claim 11 wherein:

each $Y_1$ is independently a phosphate residue, $N(R_6)_a-$ or $-CO_2R_6$;

$Y_2$ is $-N-(R_6)_b-$; and each $Y_3$ is independently a phosphate residue, $N(R_6)_a-$ or $-CO_2R_6$.

13. The compound according to claim 12 wherein:

x is 1.

14. The compound according to claim 13 wherein:

y is 2 and z is 0.

15. The compound according to claim 14 wherein:

each $Y_1$ is independently $N(R_6)_a-$ or $-CO_2R_6$; and $R_6$ is $-[R_7-X_3]_c-R_8$.

16. The compound according to claim 15 wherein:

each of $R_1$, $R_2$, $R_3$, $R_4$ and $R_7$ is independently methylene, ethylene or cyclohexylene; and each $R_8$ is independently hydrogen or alkyl of about 1 to about 16 carbons.

17. The compound according to claim 16 wherein:

a is 3; and each c is independently 0 or 1.

18. The compound according to claim 17 wherein:

b is 1.

19. The compound according to claim 18 which is N,N'-bis(dodecyloxycarbonylmethylene)-N,N'-bis(β-N,N,N-trimethylammoniumethylaminocarbonylmethylene) ethylenediamine dihalide.

20. The compound according to claim 19 wherein said halide is chloride, bromide or iodide.

21. The compound according to claim 18 which is N,N'-bis(hexadecylaminocarbonylmethylene-N,N'-bis (trimethylammoniumethylaminocarbonylmethylene) ethylenediaminedihalide.

22. The compound according to claim 21 wherein said halide is chloride, bromide or iodide.

23. The compound according to claim 17 wherein:

b is 2.

24. The compound according to claim 23 which is N,N'-bis(dodecylaminocarbonylmethylene)-N,N'-bis(β-N,N,N-trimethylammoniumethylaminocarbonylmethylene)-N,N'-dimethylethylenediamine tetrahalide.

25. The compound according to claim 24 wherein said halide is chloride, bromide or iodide.

26. The compound according to claim 23 which is N,N'-bis(dodecylaminocarbonylmethylene)-N,N'-bis(β-N,N,N-trimethylammoniumethylaminocarbonylmethylene)-N,N'-dimethylcyclohexylene-1,4-diamine tetrahalide.

27. The compound according to claim 26 wherein said halide is chloride, bromide or iodide.

28. The compound according to claim 23 which is N,N'-bis(hexadecylaminocarbonylmethylene)-N,N'-bis(β-N,N,N-trimethylaxmmoniumethylaminocarbonylmethylene)-N,N'-dimethylethylenediamine tetrahalide.

29. The compound according to claim 28 wherein said halide is chloride, bromide or iodide.

30. The compound according to claim 17 wherein:

each b is independently 1 or 2.

31. The compound according to claim 30 which is N,N'-bis(hexadecyloxycarbonylmethylene)-N-(β-N,N,N-trimethylammoniumethylaminocarbonylmethylene)-N-methyl-N'-(carboxymethylene)ethylenediamine dihalide.

32. The compound according to claim 31 wherein said halide is chloride, bromide or iodide.

33. The compound according to claim 13 wherein:

y is 2 and z is 0 or 1.

34. The compound according to claim 33 wherein:

a is 3;

b is 2;

each c is independently 0 or 1; and d is 1.

35. The compound according to claim 34 wherein:

$R_{11}$ is $-[R_7-X_3]_c-R_8$.

36. The compound according to claim 35 wherein:

each of $R_1$, $R_2$, $R_3$, $R_4$ and $R_7$ is independently methylene or ethylene; and each $R_8$ is independently hydrogen or alkyl of 1 to about 16 carbons.

37. The compound according to claim 36 which is N,N"-bis(hexadecylaminocarbonylmethylene)-N,N',N"-tris(β-N,N, N-trimethylammoniumethylaminocarbonylmethylene)-N,N',N"-trimethyldiethylenetriamine hexahalide.

38. The compound according to claim 37 wherein said halide is chloride, bromide or iodide.

39. The compound according to claim 13 wherein:

y is 3 and z is 0.

40. The compound according to claim 39 wherein:
a is 3;
b is 2;
each c is independently 0 or 1; and
d is 1.

41. The compound according to claim 40 wherein:
each of $R_1$, $R_2$, $R_3$, $R_4$ and $R_7$ is independently methylene or ethylene;
each $R_8$ is independently hydrogen or alkyl of 1 to about 16 carbons;
each of $R_9$ and $R_{10}$ is independently methylene or ethylene; and
$R_{11}$ is methyl.

42. The compound according to claim 41 which is 1,1,7,7-tetra(β-N,N,N,N-tetramethylammoniumethylaminocarbonylmethylene)-4-hexadecylaminocarbonylmethylene-N,N',N'-trimethyl-1,4,7-triazaheptane heptahalide.

43. The compound according to claim 42 wherein said halide is chloride, bromide or iodide.

44. The compound according to claim 13 wherein:
y is 3 and z is 0.

45. The compound according to claim 44 wherein:
a is 3;
b is 1;
c is 0; and
d is 1.

46. The compound according to claim 45 wherein:
each of $R_1$, $R_2$ and $R_3$ is independently methylene or ethylene;
each $R_8$ is independently hydrogen or methyl;
each of $R_9$ and $R_{10}$ is independently methylene or ethylene; and
$R_{11}$ is methyl.

47. The compound according to claim 46 which is N,N,N'',N''-tetra(β-N,N,N-trimethylammoniumethylaminocarbonyl-methylene)-N'-(1,2-dioleoylglycero-3-phosphoethanolaminocarbonylmethylene) diethylenetriamine tetrahalide.

48. The compound according to claim 47 wherein said halide is chloride, bromide or iodide.

49. A cationic lipid composition comprising the cationic lipid compound according to claim 1.

50. The cationic lipid composition according to claim 49 wherein said composition is lyophilized.

51. The cationic lipid composition according to claim 49 which is selected from the group consisting of micelles, liposomes and mixtures thereof.

52. The cationic lipid composition according to claim 51 further comprising an amphipathic compound for stabilizing the composition.

53. The cationic lipid composition according to claim 52 further comprising a gas, a precursor to a gas or a mixture thereof.

54. The cationic lipid composition according to claim 53 wherein said gas or said precursor to a gas is selected from the group consisting of perfluoromethane, perfluoroethane, perfluoropropane, perfluorobutane, perfluorocyclobutane, perfluoropentane, perfluorohexane, and mixtures thereof.

55. The cationic lipid composition according to claim 53 which comprises a mixture of a gas and a precursor to a gas.

56. The cationic lipid composition according to claim 54 wherein said gas or gaseous precursor further comprises nitrogen.

57. The cationic lipid composition according to claim 49 further comprising a gas, a precursor to a gas, or a mixture thereof, and an amphipathic compound for stabilizing the composition.

58. The cationic lipid composition according to claim 57 wherein said amphipathic compound comprises a lipid.

59. The cationic lipid composition according to claim 58 which is selected from the group consisting of suspensions, emulsions, and vesicle compositions.

60. The cationic lipid composition according to claim 59 which comprises a cationic vesicle composition.

61. The cationic vesicle composition according to claim 60 wherein said vesicles are selected from the group consisting of unilamellar vesicles, oligolamellar vesicles and multilamellar vesicles.

62. The cationic vesicle composition according to claim 61 wherein said lipid is a polymerizable lipid.

63. The cationic vesicle composition according to claim 61 further comprising polyethyleneglycol.

64. The cationic vesicle composition according to claim 61 wherein said vesicles comprise unilamellar vesicles.

65. The cationic vesicle composition according to claim 64 wherein said vesicles comprise a monolayer.

66. The cationic vesicle composition according to claim 65 wherein said lipid is a phospholipid and said gas or said precursor to a gas is sulfur hexafluoride.

67. The cationic vesicle composition according to claim 65 wherein said lipid is a phospholipid and said gas or gaseous precursor is perfluoropentane.

68. The cationic vesicle composition according to claim 65 wherein said lipid is a phospholipid and said gas or gaseous precursor is perfluoropropane.

69. The cationic vesicle composition according to claim 64 wherein said vesicles comprise a bilayer.

70. The cationic vesicle composition according to claim 69 wherein said lipid is a phospholipid and said gas or gaseous precursor is sulfur hexafluoride.

71. The cationic vesicle composition according to claim 69 wherein said lipid is a phospholipid and said gas or gaseous precursor is perfluoropentane.

72. The cationic vesicle composition according to claim 69 wherein said lipid is a phospholipid and said gas or gaseous precursor is perfluoropropane.

73. The cationic vesicle composition according to claim 59 wherein said vesicles are selected from the group consisting of oligolamellar and multilamellar vesicles.

74. The cationic vesicle composition according to claim 73 wherein said vesicles comprise monolayers.

75. The cationic vesicle composition according to claim 74 wherein said lipid is a phospholipid and said gas or gaseous precursor is sulfur hexafluoride.

76. The cationic vesicle composition according to claim 74 wherein said lipid is a phospholipid and said gas or said precursor to a gas is perfluoropentane.

77. The cationic vesicle composition according to claim 74 wherein said lipid is a phospholipid and said gas or gaseous precursor is perfluoropropane.

78. The cationic vesicle composition according to claim 73 wherein said vesicles comprise bilayers.

79. The cationic vesicle composition according to claim 78 wherein said lipid is a phospholipid and said gas or gaseous precursor is sulfur hexafluoride.

80. The cationic vesicle composition according to claim 78 wherein said lipid is a phospholipid and said gaseous precursor is perfluoropentane.

81. The cationic vesicle composition according to claim 78 wherein said lipid is a phospholipid and said gaseous precursor is perfluoropropane.

82. The cationic lipid composition according to claim 58 wherein said lipids comprise unilamellar lipids, oligolamellar lipids or multilamellar lipids.

83. The cationic lipid composition according to claim 82 wherein said lipids are polymerizable lipids.

84. The cationic lipid composition according to claim 82 further comprising polyethyleneglycol.

85. The cationic lipid composition according to claim 82 wherein said lipids comprise unilamellar lipids.

86. The cationic lipid composition according to claim 85 wherein said lipids are in the form of a monolayer.

87. The cationic lipid composition according to claim 86 wherein said lipids are phospholipids and said gas or gaseous precursor is sulfur hexafluoride.

88. The cationic lipid composition according to claim 86 wherein said lipids are phospholipids and said gas or gaseous precursor is perfluoropentane.

89. The cationic lipid composition according to claim 86 wherein said lipids are phospholipids and said gas or gaseous precursor is perfluoropropane.

90. The cationic lipid composition according to claim 85 wherein said lipids are in the form of a bilayer.

91. The cationic lipid composition according to claim 90 wherein said lipids are phospholipids and said gas or gaseous precursor is sulfur hexafluoride.

92. The cationic lipid composition according to claim 90 wherein said lipids are phospholipids and said gas or gaseous precursor is perfluoropentane.

93. The cationic lipid composition according to claim 90 wherein said lipids are phospholipids and said gas or gaseous precursor is perfluoropropane.

94. The cationic lipid composition according to claim 82 wherein said lipids comprise oligolamellar lipids or multilamellar lipids.

95. The cationic lipid composition according to claim 94 wherein said lipids are in the form of monolayers.

96. The cationic lipid composition according to claim 95 wherein said lipids are phospholipids and said gas or gaseous precursor is sulfur hexafluoride.

97. The cationic lipid composition according to claim 95 wherein said lipids are phospholipids and said gas or gaseous precursor is perfluoropentane.

98. The cationic lipid composition according to claim 95 wherein said lipids are phospholipids and said gas or gaseous precursor is perfluoropropane.

99. The cationic lipid composition according to claim 94 wherein said lipids are in the form of bilayers.

100. The cationic lipid composition according to claim 99 wherein said lipids are phospholipids and said gas or gaseous precursor is sulfur hexafluoride.

101. The cationic lipid composition according to claim 99 wherein said lipids are phospholipids and said gas or gaseous precursor is perfluoropentane.

102. The cationic lipid composition according to claim 99 wherein said lipids are phospholipids and said gas or gaseous precursor is perfluoropropane.

103. A cationic lipid formulation for the intracellular delivery of a bioactive agent comprising, in combination with a bioactive agent, a cationic lipid composition which comprises the cationic lipid compound according to claim 1.

104. The lipis formulation according to claim 103 wherein said bioactive agent comprises genetic material.

105. The lipid formulation according to claim 103 which is selected from the group consisting of micelles, liposomes and mixtures thereof.

106. The lipid formulation according to claim 105 comprising said bioactive agent entrapped within said micelles or liposomes.

107. The lipid formulation according to claim 103 further comprising a gas, a gaseous precursor or a mixture thereof.

108. The lipid formulation according to claim 107 wherein said gas, gaseous precursor or mixture thereof is selected from the group consisting of perfluoromethane, perfluoroethane, perfluoropropane, perfluorobutane, perfluorocyclobutane, perfluoropentane, perfluorohexane and mixtures thereof.

109. The lipid formulation according to claim 108 wherein said gas, gaseous precursor or mixture thereof further comprises nitrogen.

110. The process for the preparation of a cationic lipid formulation for the intracellular delivery of a bioactive agent comprising combining together a bioactive agent and a cationic lipid composition which comprises the cationic lipid compound according to claim 1.

111. The process according to claim 110 wherein said bioactive agent comprises genetic material.

112. The process according to claim 110 wherein said formulation is lyophilized.

113. The process according to claim 110 wherein said composition is selected from the group consisting of micelles, liposomes and mixtures thereof.

114. The process according to claim 113 comprising entrapping said bioactive agent within said micelles or liposomes.

115. The process according to claim 110 wherein said composition further comprises a gas, a gaseous precursor or a mixture thereof.

116. The process according to claim 115 wherein said gas, gaseous precursor or mixture thereof is selected from the group consisting of perfluoromethane, perfluoroethane, perfluoropropane, perfluorobutane, perfluorocyclobutane, perfluoropentane, perfluorohexane and mixtures thereof.

117. The process according to claim 116 wherein said gas, gaseous precursor or mixture thereof further comprises nitrogen.

118. A method for delivering intracellularly a bioactive agent comprising contacting a cell with a cationic lipid composition which comprises the cationic lipid compound according to claim 1 and the bioactive agent.

119. The method according to claim 118 wherein said composition is reconstituted from a lyophilized composition.

120. The method of claim 118 wherein said composition is selected from the group consisting of micelles, liposomes and mixtures thereof.

121. The method of claim 120 comprising said bioactive agent entrapped within said micelles or liposomes.

122. The method of claim 118 wherein said bioactive agent comprises genetic material.

123. The method of claim 122 wherein said genetic material is selected from the group consisting of polynucleotide, DNA, RNA, polypeptide and mixtures thereof.

124. The method according to claim 118 wherein said composition further comprises a gas, a gaseous precursor or a mixture thereof.

125. The method according to claim 124 wherein said gas, gaseous precursor or mixture thereof is selected from the group consisting of perfluoromethane, perfluoroethane, perfluoropropane, perfluorobutane, perfluorocyclobutane, perfluoropentane, perfluorohexane and mixtures thereof.

126. The method according to claim 125 wherein said gas, gaseous precursor or mixture thereof further comprises nitrogen.

127. The cationic vesicle comprising a cationic lipid compound according to claim 1 and a gas or gaseous precursor.

128. The cationic vesicle according to claim 127 which is selected from the group consisting of unilamellar vesicles, oligolamellar vesicles and multilamellar vesicles.

129. The cationic vesicle according to claim 128 which comprises unilamellar vesicles.

130. The cationic vesicle according to claim 129 which comprises a monolayer.

131. The cationic vesicle according to claim 129 which comprises a bilayer.

132. The cationic vesicle according to claim 128 which is selected from the group consisting of oligolamellar vesicles and multilamellar vesicles.

133. The cationic vesicle according to claim 132 which comprises monolayers.

134. The cationic vesicle according to claim 132 which comprises bilayers.

135. The cationic vesicle according to claim 132 further comprising an amphipathic compound for stabilizing the vesicle.

136. The cationic vesicle according to claim 135 wherein said amphipathic compound comprises a lipid.

137. The cationic vesicle according to claim 136 wherein said lipid is a phospholipid and said gas or gaseous precursor is sulfur hexafluoride.

138. The cationic vesicle according to claim 136 wherein said lipid is a phospholipid and said gas or gaseous precursor is perfluoropentane.

139. The cationic vesicle according to claim 136 wherein said lipid is a phospholipid and said gas or gaseous precursor is perfluoropropane.

140. The cationic vesicle according to claim 136 wherein said lipid is a polymerizable lipid.

141. The cationic vesicle according to claim 136 further comprising polyethyleneglycol.

142. A cationic lipid compound of the formula

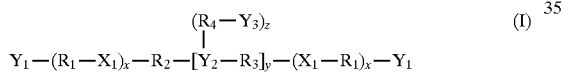

(I)

wherein:

each of x, y and z is independently an integer from 0 to about 100;

each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—;

each $X_2$ is independently O or S;

each $Y_1$ is independently a phosphate residue, N($R_6$)$_a$—, S($R_6$)$_a$—, P($R_6$)$_a$— or —$CO_2R_6$, wherein a is an integer from 1 to 3;

each $Y_2$ is independently —N($R_6$)$_b$—, —S($R_6$)$_b$— or —P($R_6$)$_b$—, wherein b is an integer from 0 to 2;

each $Y_3$ is independently a phosphate residue, N($R_6$)$_a$—, S($R_6$)$_a$—, P($R_6$)$_a$— or —$CO_2R_6$, wherein a is an integer from 1 to 3;

each of $R_1$, $R_2$, $R_3$ and $R_4$ is independently alkylene of 1 to about 20 carbons;

each $R_5$ is independently hydrogen or alkyl of 1 to about 10 carbons; and each $R_6$ is independently —[$R_7$—$X_3$]$_c$—$R_8$ or —$R_9$—[$X_4$—$R_{10}$]$_d$—Q, wherein:

each of c and d is independently an integer from 0 to about 100;

each Q is independently a phosphate residue, —N($R_{11}$)$_q$, —S($R_{11}$)$_q$, —P($R_{11}$)$_q$ or —$CO_2R_6$, wherein q is an integer from 1 to 3;

each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—;

each $R_7$ is independently alkylene of 1 to about 20 carbons;

each $R_8$ is independently hydrogen or alkyl of 1 to about 40 carbons;

each of $R_9$ and $R_{10}$ is independently alkylene of 1 to about 20 carbons; and each $R_{11}$ is independently —[$R_7$—$X_3$]$_c$—$R_8$ or —$R_9$—[$X_4$—$R_{10}$]$_d$—W, wherein:

each W is independently a phosphate residue, —N($R_{12}$)$_w$, —S($R_{12}$)$_w$, —P($R_{12}$)$_w$, or —$CO_2R_6$, wherein w is an integer from 1 to 3; and $R_{12}$ is —[$R_7$—$X_3$]$_c$—$R_8$; with the proviso that the compound of formula (I) comprises at least one quaternary salt.

143. The compound according to claim 142 wherein said compound is in lyophilized form.

* * * * *

UNITED STATES PATENT AND TRADEMARK OFFICE
CERTIFICATE OF CORRECTION

PATENT NO.    : 5,830,430
DATED         : Nov. 3, 1998
INVENTOR(S)   : Unger et al.

It is certified that error appears in the above-indentified patent and that said Letters Patent is hereby corrected as shown below:

On the cover page, second column, under "OTHER PUBLICATIONS", at "Villanueva et al.", please delete "Patters" and insert --Patterns-- therefor.

On the cover page, second column, under "OTHER PUBLICATIONS", at "Keller et al.", second line thereof, please delete "Microcirulation" and insert --Microcirculation-- therefor.

On page 5, first column, under "OTHER PUBLICATIONS", at "Shiina et al.", please delete "Hyperthermiaby" and insert --Hyperthermia by-- therefor.

On page 5, first column, under "OTHER PUBLICATIONS", at "Poznansky et al.", please delete "Biologica" and insert --Biological-- therefor.

On page 5, second column, under "OTHER PUBLICATIONS", at "Ter-Pogossia", please delete "Ter-Pogossia" and insert --Ter-Pogossian,-- therefor.

On page 5, second column, under "OTHER PUBLICATIONS", at "San", please delete "Toxicitiy" and insert --Toxicity-- therefor.

On page 6, first column, under "OTHER PUBLICATIONS", at "Behr, J.", second line thereof, please delete "lipopolyamine-caoted" and insert --lipopolyamine-coated" therefor.

UNITED STATES PATENT AND TRADEMARK OFFICE
CERTIFICATE OF CORRECTION

PATENT NO. : 5,830,430
DATED : Nov. 3, 1998
INVENTOR(S) : Unger et al.

It is certified that error appears in the above-indentified patent and that said Letters Patent is hereby corrected as shown below:

On page 6, second column, under "OTHER PUBLICATIONS", at "Stel'mashok et al.", please delete "Stel'mashok" and insert --Stelmashok-- therefor.

In column 3, line 18, please delete "$_{or}-_{CO2}R_6$," and insert --or $CO_2R_6$,-- therefor.

In column 3, line 51, please delete "—$[R_7—X_3]_{c—R8}$" and insert -- —$[R_7—X_3]_c—R_8$-- therefor.

In column 5, line 5, please delete "$R_{11}$, is" and insert --$R_{11}$ is-- therefor.

In column 6, line 49, please delete "rylthio" and insert --arylthio-- therefor.

In column 9, line 3, please delete "generally, concentric" and insert --generally concentric-- therefor.

In column 12, line 35, please delete "—C(=O)—$NR_6$—" and insert -- —C(=O)—$NR_5$— -- therefor.

In column 14, line 62, please delete "$[X_4—R_1]_d—Q$" and insert -- $[X_4—R_{10}]_d—Q$ -- therefor.

In column 19, line 60, please delete "*Macro molecular*" and insert --*Macromolecular*-- therefor.

UNITED STATES PATENT AND TRADEMARK OFFICE
CERTIFICATE OF CORRECTION

PATENT NO. : 5,830,430  
DATED : Nov. 3, 1998  
INVENTOR(S) : Unger et al.

Page 3 of 6

It is certified that error appears in the above-indentified patent and that said Letters Patent is hereby corrected as shown below:

In column 20, line 55, please delete "resent" and insert --present-- therefor.

In column 20, lines 57-58, please delete "fluoro surfactant" and insert --fluorosurfactant-- therefor.

In column 22, line 5, please delete "quipment" and insert --equipment-- therefor.

In column 22, line 9, please delete "ompositions" and insert --compositions-- therefor.

In column 22, line 9, please delete "resent" and insert --present-- therefor.

In column 27, line 5, please delete "intra ocular" and insert --intraocular-- therefor.

In column 27, line 5, please delete "trans epithelial" and insert --transepithelial-- therefor.

In column 29, line 29, please delete "(dodecylaminocarbonylmethylene)-N,N-'-bis" and insert --(dodecylaminocarbonylmethylene)-N,N'-bis-- therefor.

In column 30, line 35, please delete "0.59" and insert --0.5%-- therefor.

In column 30, line 61, please delete "(hexadecylaminocarbonylmethylene)-N,N'N''-tris(β-" and insert -- (hexadecylaminocarbonylmethylene)-N,N',N''-tris(β- -- therefor.

UNITED STATES PATENT AND TRADEMARK OFFICE
CERTIFICATE OF CORRECTION

PATENT NO. : 5,830,430
DATED : Nov. 3, 1998
INVENTOR(S) : Unger et al.

It is certified that error appears in the above-indentified patent and that said Letters Patent is hereby corrected as shown below:

In column 35, line 17, please delete "0°-50° C" and insert --0°-5° C-- therefor.

In column 38, line 57, please delete "CAT ELISAT™" and insert --CAT ELISA™-- therefor.

In column 42, line 57, claim 2, please delete "claim 1" and insert -- claim 142 -- therefor.

In column 42, line 66, claim 4, please delete "claim 1" and insert -- claim 142 -- therefor.

In column 43, line 1, claim 5, please delete "claim 1" and insert -- claim 142 -- therefor.

In column 43, line 48, claim 12, please delete "claim 11" and insert -- claim 142 -- therefor.

In column 44, line 14, claim 21, please delete "ethylenediaminedihalide" and insert --ethylenediamine dihalide-- therefor.

In column 44, line 34, claim 28, please delete "N-trimethylaxmmoniumethylamino-carbonylmethylene)-N" and insert --N-trimethylammoniummethylaminocarbonylmethylene)-N therefor.

In column 45, line 18, claim 42, please delete "hexadecylaminocarbonylmethylene-N,N',N'-trimethyl-1,4" and insert --hexadecylaminocarbonylmethylene-N,N',N''-trimethyl-1,4-- therefor.

UNITED STATES PATENT AND TRADEMARK OFFICE
CERTIFICATE OF CORRECTION

PATENT NO. : 5,830,430
DATED : Nov. 3, 1998
INVENTOR(S) : Unger et al.

It is certified that error appears in the above-indentified patent and that said Letters Patent is hereby corrected as shown below:

In column 45, line 46, claim 49, please delete "claim 1" and insert -- claim 142 -- therefor.

In column 46, line 16, claim 62, please delete "polymerizable" and insert --polymerizable-- therefor.

In column 47, line 59, claim 103, please delete "claim 1" and insert -- claim 142 -- therefor.

In column 47, line 60, claim 104, please delete "lipis" and insert --lipid-- therefor.

In column 48, line 12, claim 110, please delete "The process for" and insert --A process for-- therefor.

In column 48, line 15, claim 110, please delete "claim 1" and insert -- claim 142 -- therefor.

In column 48, line 39, claim 118, please delete "claim 1" and insert -- claim 142 -- therefor.

UNITED STATES PATENT AND TRADEMARK OFFICE
CERTIFICATE OF CORRECTION

PATENT NO.   : 5,830,430
DATED        : Nov. 3, 1998
INVENTOR(S)  : Unger et al.

It is certified that error appears in the above-indentified patent and that said Letters Patent is hereby corrected as shown below:

In column 48, line 66, claim 127, please delete "claim 1" and insert -- claim 142 -- therefor.

Signed and Sealed this

Twenty-third Day of November, 1999

Attest:

Q. TODD DICKINSON

*Attesting Officer*            *Acting Commissioner of Patents and Trademarks*